United States Patent
Shitara

(10) Patent No.: US 11,231,363 B2
(45) Date of Patent: Jan. 25, 2022

(54) QUALITY MEASUREMENT METHOD AND QUALITY MEASUREMENT DEVICE FOR LONG SHEET MATERIAL

(71) Applicants: PSM INTERNATIONAL, INC., Tokyo (JP); PROCEMEX OY, Jyskae (FI)

(72) Inventor: Hisataka Shitara, Tokyo (JP)

(73) Assignees: PSM INTERNATIONAL, INC., Tokyo (JP); PROCEMEX OY, Jyväskylä (FI)

( * ) Notice: Subject to any disclaimer, the term of this patent is extended or adjusted under 35 U.S.C. 154(b) by 0 days.

(21) Appl. No.: 17/059,629

(22) PCT Filed: May 31, 2018

(86) PCT No.: PCT/JP2018/020910
§ 371 (c)(1),
(2) Date: Nov. 30, 2020

(87) PCT Pub. No.: WO2019/229919
PCT Pub. Date: Dec. 5, 2019

(65) Prior Publication Data
US 2021/0223171 A1     Jul. 22, 2021

(51) Int. Cl.
*H04N 5/225* (2006.01)
*G01N 21/47* (2006.01)
*G01N 21/3559* (2014.01)

(52) U.S. Cl.
CPC ......... *G01N 21/47* (2013.01); *G01N 21/3559* (2013.01); *H04N 5/2256* (2013.01)

(58) Field of Classification Search
CPC ... G01N 21/47; G01N 21/3559; H04N 5/2256
See application file for complete search history.

(56) References Cited

U.S. PATENT DOCUMENTS

| 6,355,931 B1* | 3/2002 | Hernandez | D21F 7/003 250/339.1 |
| 6,504,617 B2* | 1/2003 | Komulainen | G01B 11/303 356/446 |

(Continued)

FOREIGN PATENT DOCUMENTS

| EP | 0604875 A2 | 7/1994 |
| EP | 0604875 A3 | 1/1995 |

(Continued)

OTHER PUBLICATIONS

Infrared sensor for automated inspection of hot metal surface; Setzer et al.; Proceedings of SPIE; 1990; retrieved Nov. 16, 2021 (Year: 1990).*

(Continued)

*Primary Examiner* — Jonathan R Messmore
(74) *Attorney, Agent, or Firm* — Bacon & Thomas, PLLC

(57) ABSTRACT

The quality measurement method for a long sheet material W includes measuring cellulose fibers, % moisture, and % ash of the paper web W by using area cameras 1102 to 1106 having an infrared light receiving element and a light source 1100 having an infrared light emitting LED element. Performance check for the infrared cameras 1102 to 1106 over the entire width and correction of measured values are performed by using consistency between measured values for the same point in an overlap area measured by adjacent cameras and reference samples 1107 at the off-sheet positions provided at both sides.

6 Claims, 20 Drawing Sheets

(56) References Cited

U.S. PATENT DOCUMENTS

| | | | | |
|---|---|---|---|---|
| 2014/0184784 A1* | 7/2014 | Yanase | ............... | G01N 21/8803 348/92 |
| 2015/0292155 A1 | 10/2015 | Bomstad et al. | | |
| 2017/0270381 A1* | 9/2017 | Itoh | ....................... | B60S 1/0844 |
| 2018/0202924 A1* | 7/2018 | Harigaya | ............. | A61B 5/4842 |
| 2019/0129396 A1 | 5/2019 | Valkonen | | |
| 2020/0217805 A1* | 7/2020 | Sugiura | ................ | H04N 5/2353 |
| 2021/0164785 A1* | 6/2021 | Dooley | .................... | H04N 5/33 |

FOREIGN PATENT DOCUMENTS

| | | |
|---|---|---|
| FI | 20165387 A | 11/2017 |
| JP | 2002544475 A | 12/2002 |
| JP | 2004277899 A | 10/2004 |
| JP | 2004294129 A | 10/2004 |
| JP | 2004361149 A | 12/2004 |
| JP | 2008064686 A | 3/2008 |
| JP | 2013130529 A | 7/2013 |
| JP | 2015002241 A | 1/2015 |
| JP | 2018104838 A | 7/2018 |
| WO | WO2013147038 A1 | 10/2013 |
| WO | WO2017191363 A1 | 11/2017 |

OTHER PUBLICATIONS

Detection of surface defects on sheet metal parts by using one-shot deflectometry in the infrared image; Sarosi et al.; ETH Zurich; 2010; retrieved Nov. 16, 2021 (Year: 2010).*

Japanese Journal of Paper Technology, vol. 37, pp. 9-14 (Aug. 1, 1994), with partial English translation.

EESR dated Nov. 29, 2021 in corresponding European Patent Appln. No. 18921132.9.

* cited by examiner

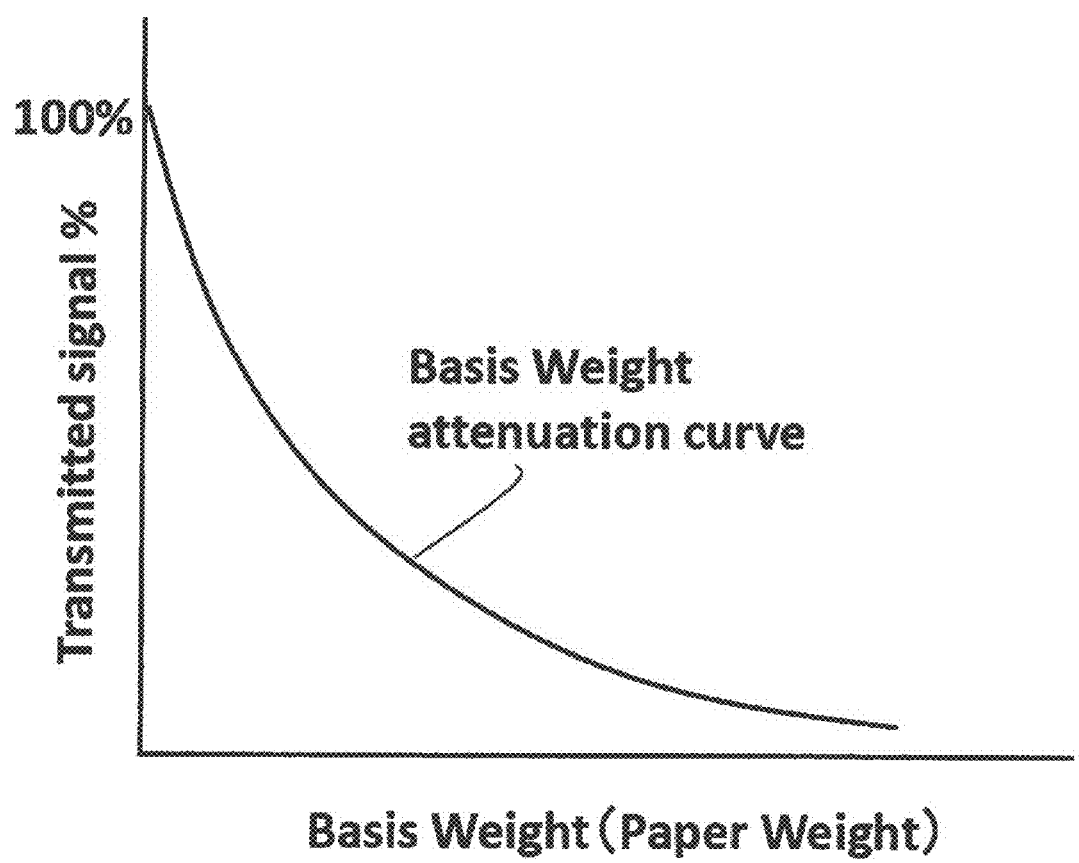

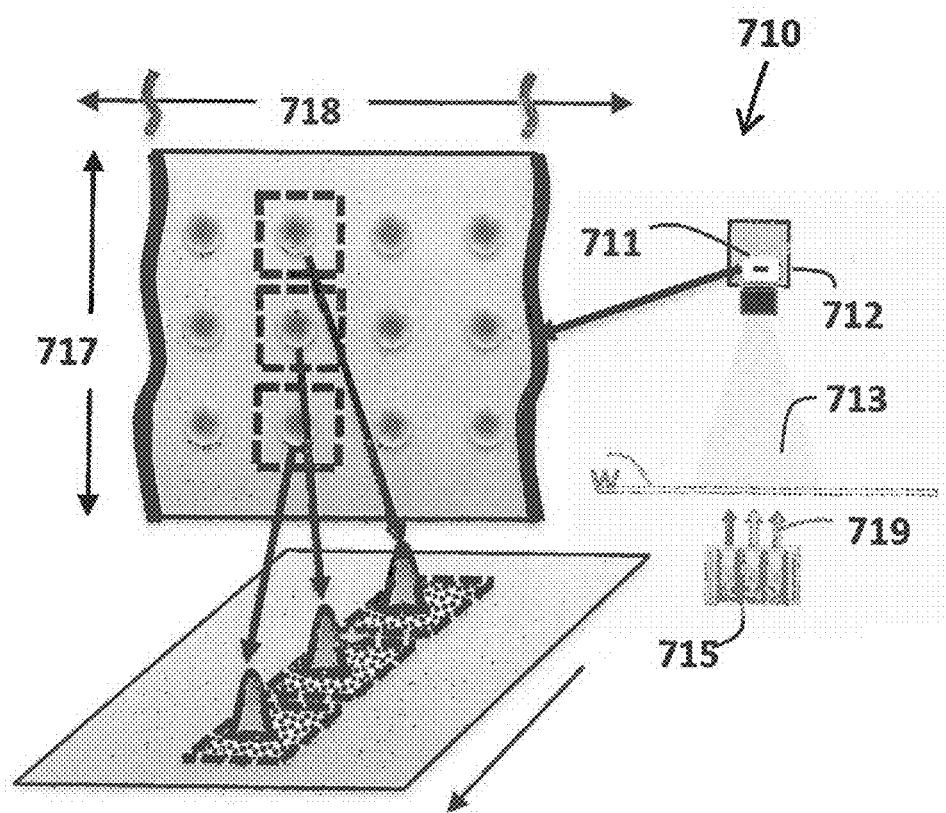

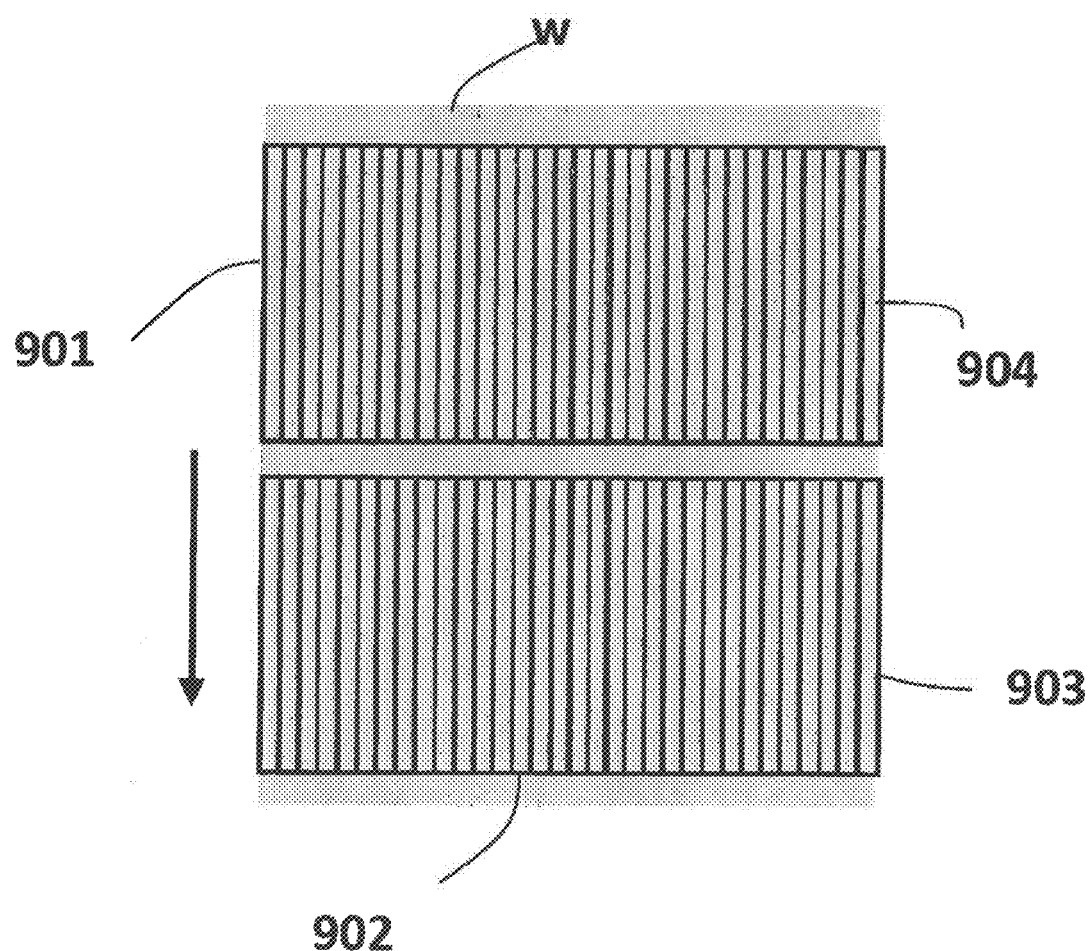

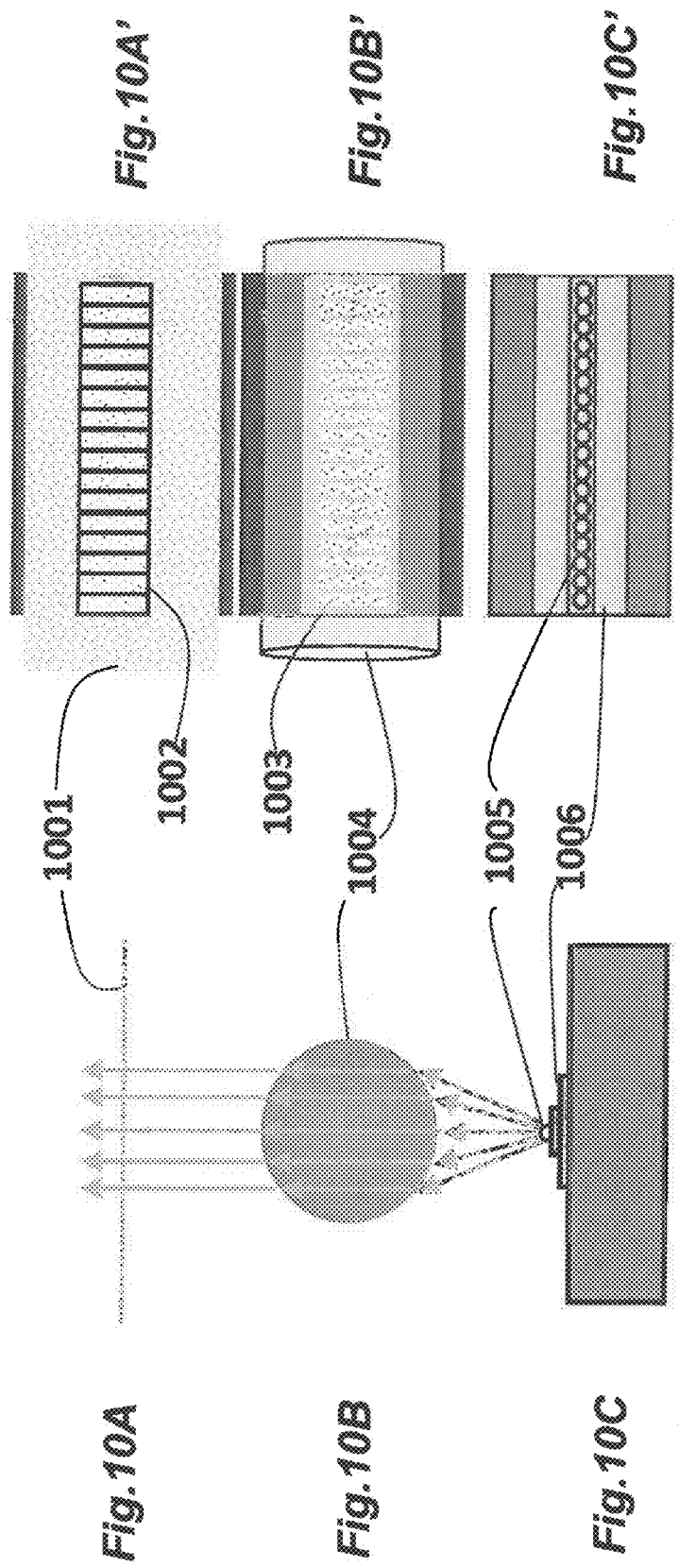

*Fig.11A*
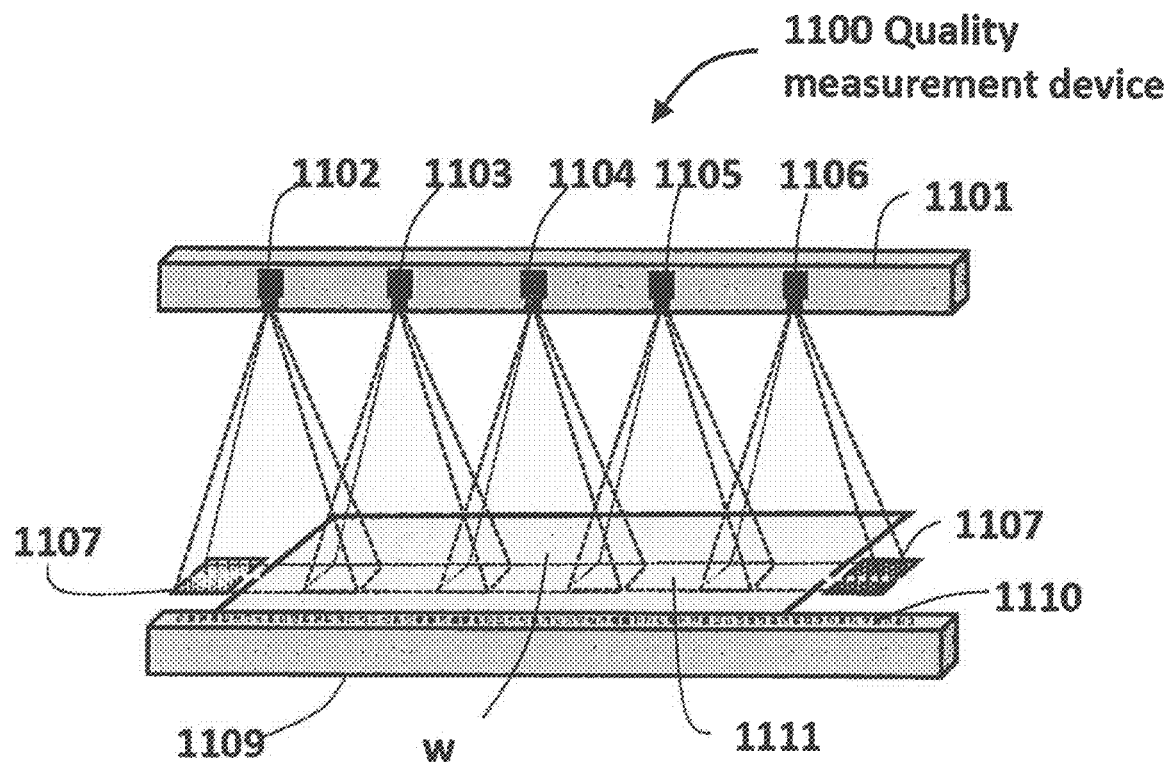
*Fig.11B*  *Fig.11C*
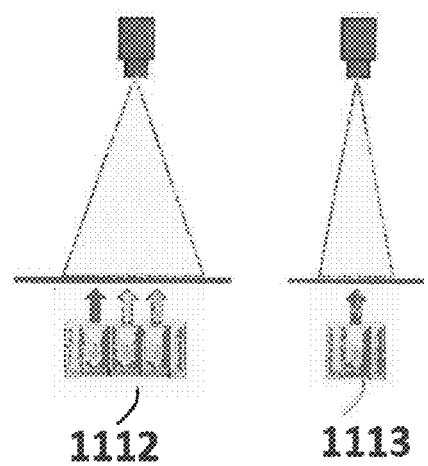

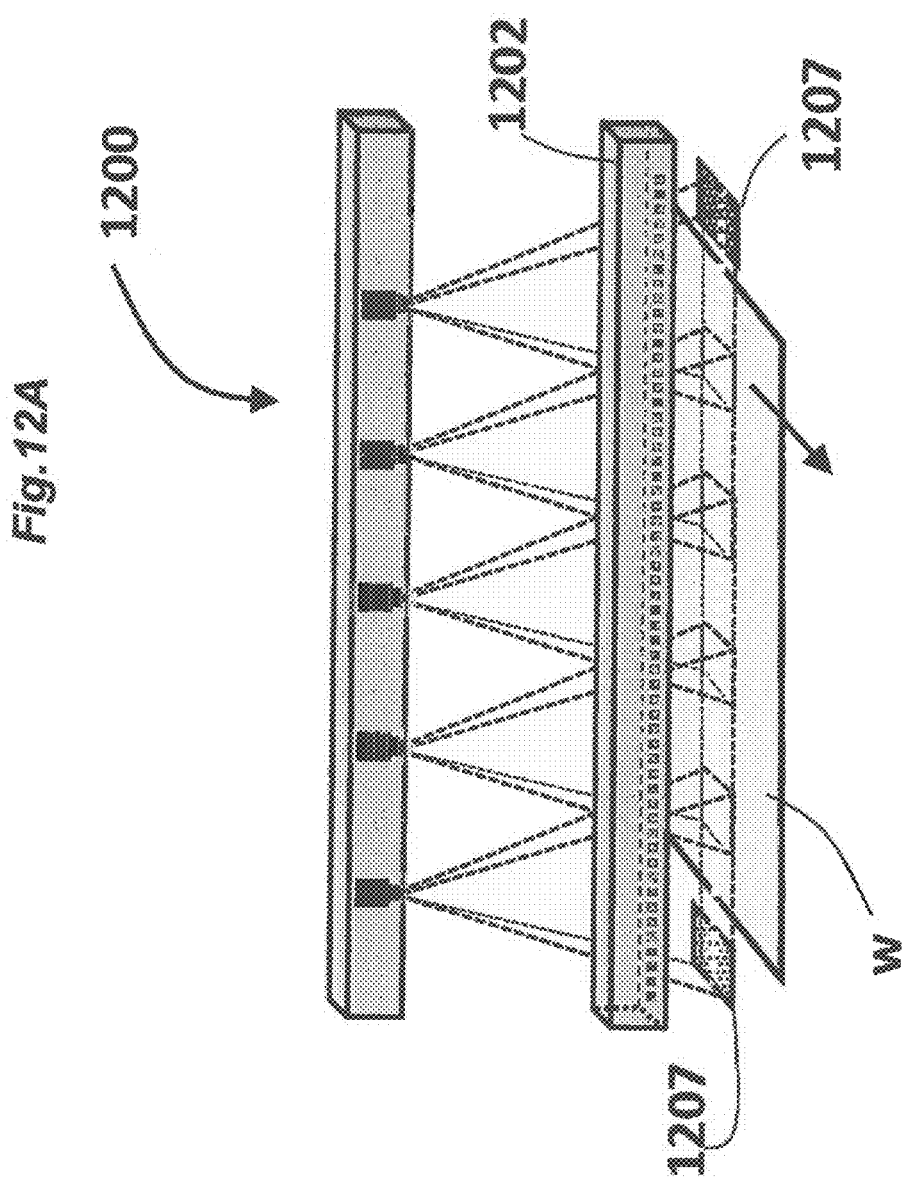
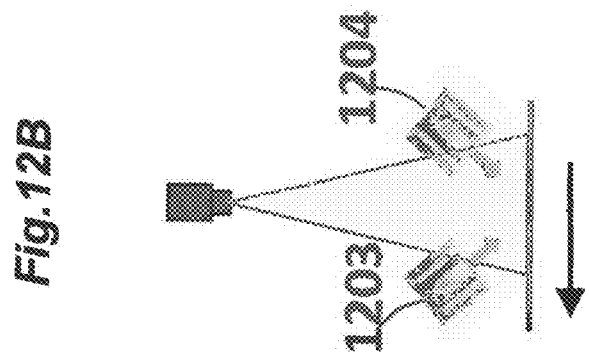
Fig. 12A
Fig. 12B

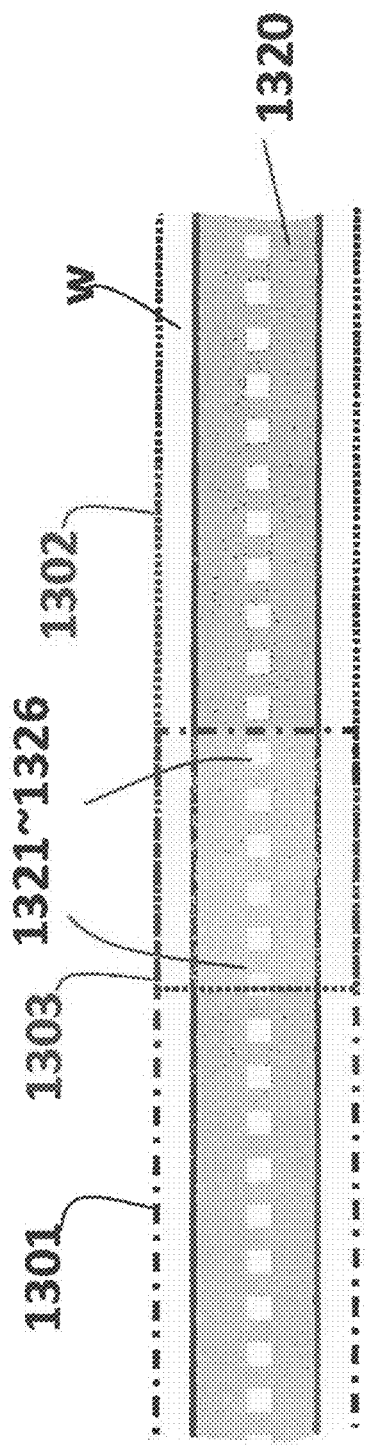
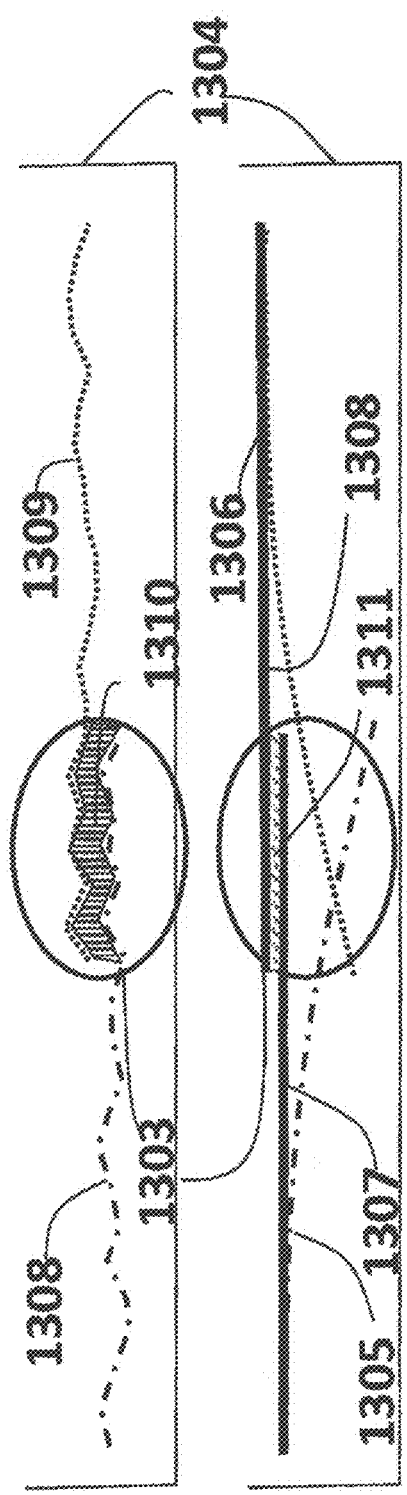
Fig.13A
Fig.13B
Fig.13C

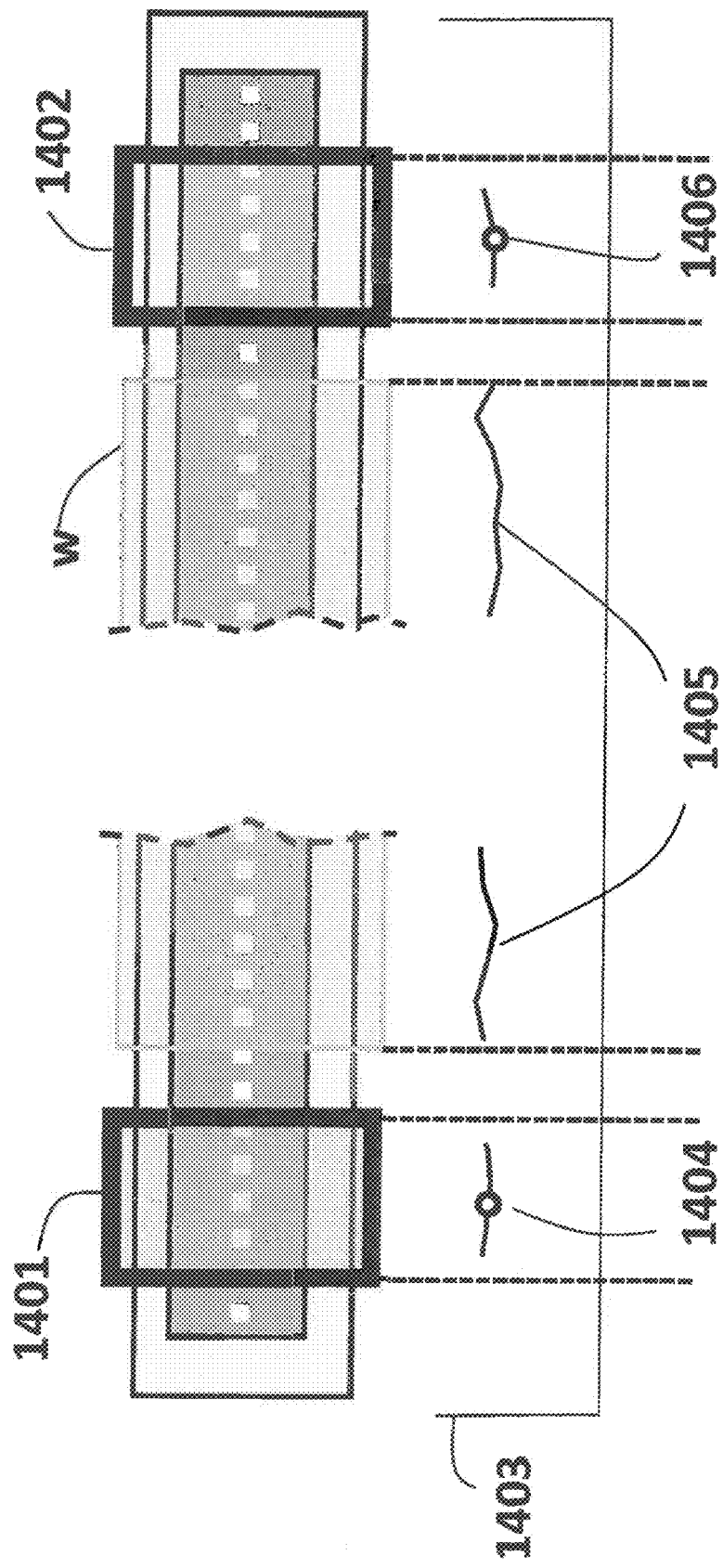

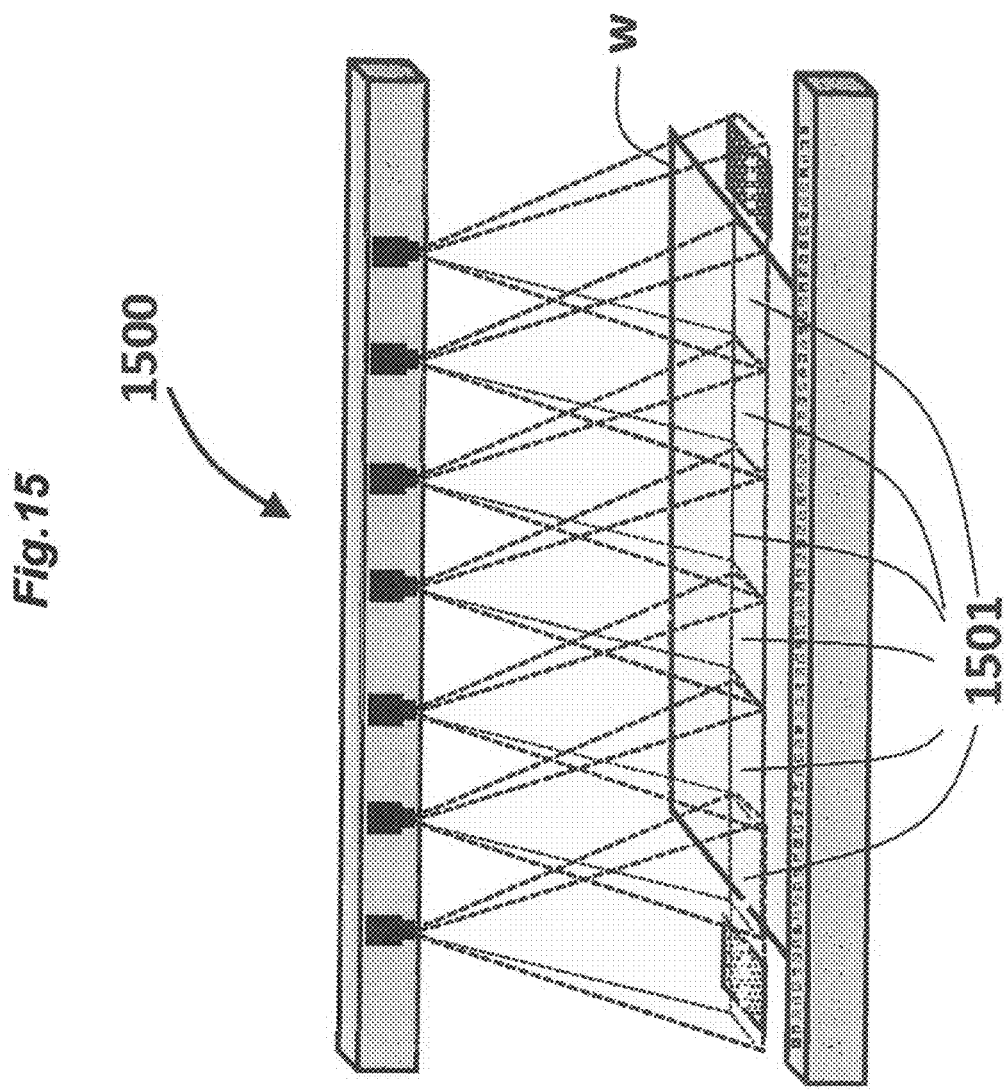

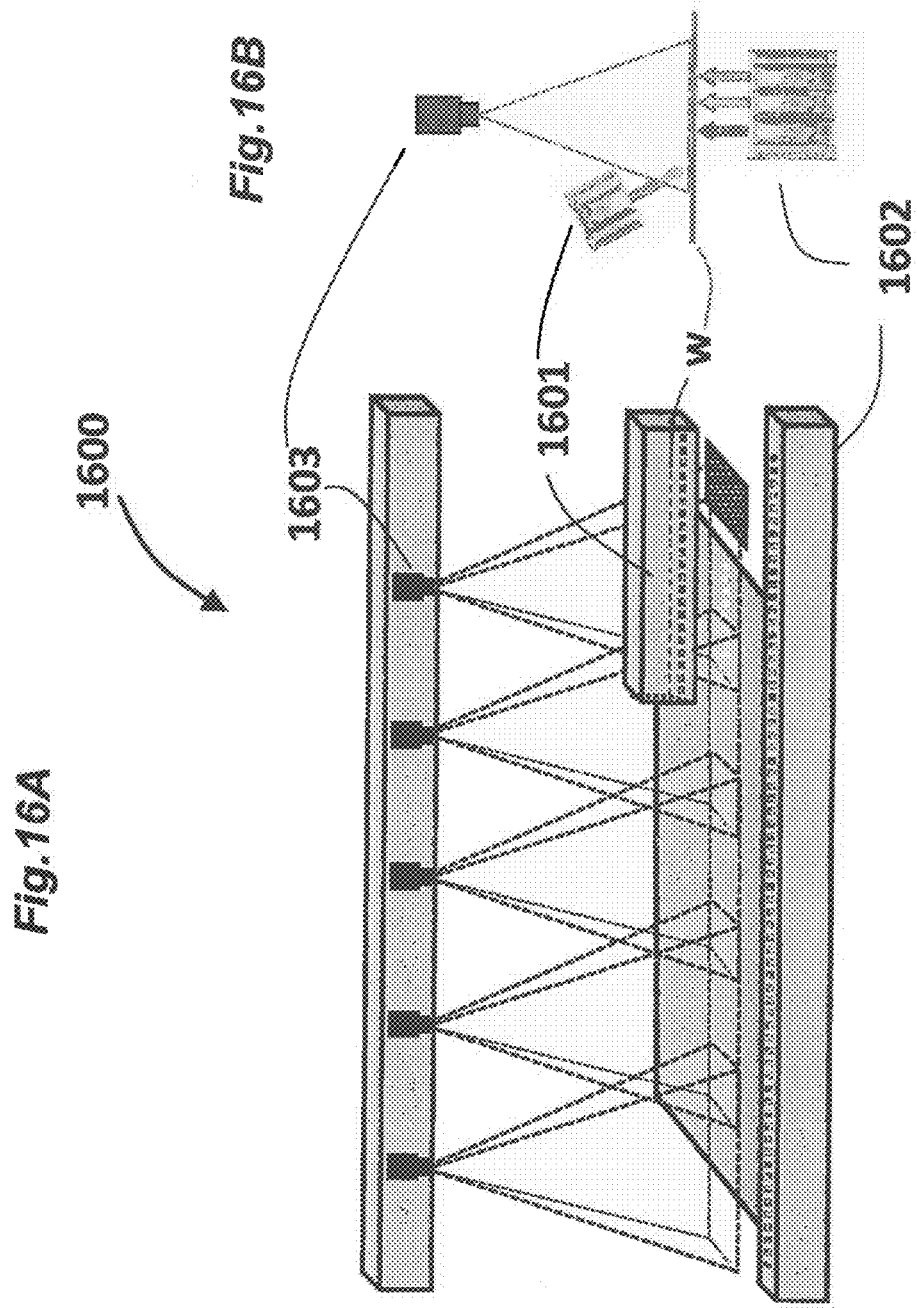

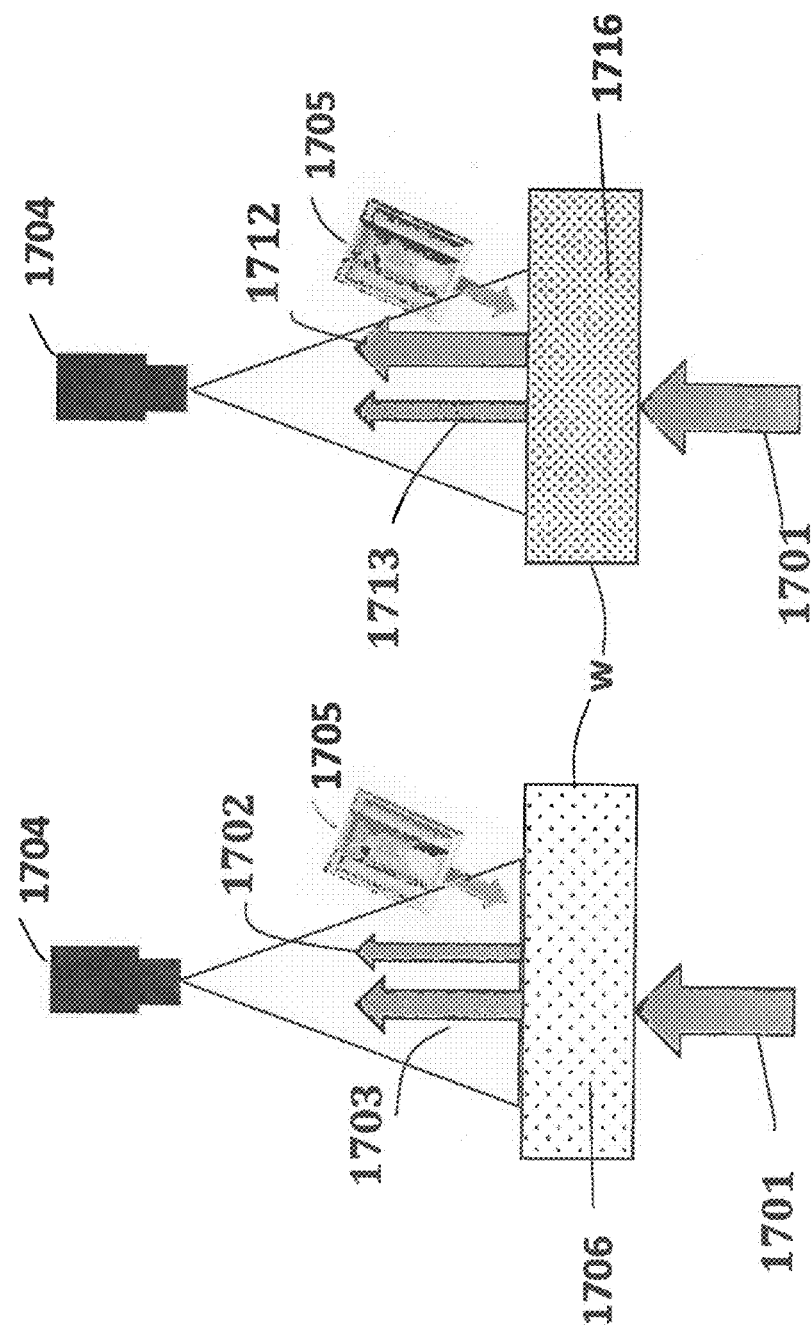

QUALITY MEASUREMENT METHOD AND QUALITY MEASUREMENT DEVICE FOR LONG SHEET MATERIAL

TECHNICAL FIELD

The present invention relates to a quality measurement method for a long sheet material, such as a paper web (rolled paper) or a plastic film manufactured in a paper machine or the like, and particularly relates to a quality measurement method without using scanning and a quality measurement device.

BACKGROUND ART

A long sheet material such as paper web or the like produced by using a paper machine is wound on a reel spool. Unlike webs in which raw materials thereof evenly distributed, such as metal sheets and plastic films, paper webs have a structure in which cellulose fibers as raw materials, and filler and water for connecting the cellulose fibers, increasing paper strength, and causing light scattering are intermingled. Thus, in a cutaway view of such a paper web, relatively large vacant spaces are observed (see FIG. 1). Quality Control System (QCS) is used in most paper machines because paper is sold mainly by weight. Sensors for measuring quality used in QCS include a basis weight sensor using a radiation source, a % moisture sensor using infrared, and an ash sensor using X-rays. Unlike other long sheet materials to be controlled based on their thickness, paper webs are measured by using various sensors. This is because moisture contained in a paper web can freely get in and out from the paper web, even after the paper web is formed into a sheet. Difficulty in measurement and quality control in the paper web is resulted from the moisture content.

In paper machines that manufacture various grades of paper with widths ranging from 1 m to 10 m and manufacturing speed ranging from several meters to 2000 m per minute, almost all of sensors for measuring quality parameters are housed in a sensor head mounted on a device referred to as a scanner. These sensors are used to measure the paper weight (basis weight), % moisture, thickness (caliper), % ash, etc. As in a common paper machine illustrated in FIG. 2 and a paper machine described in PTL 1, a scanning sensor for a paper web is provided immediately before a reel and is used as control criteria for manufacture. Depending on the process, a scanning sensor may also be installed before applying a coating to the surface of the paper. These paper quality parameters can be controlled. The basis weight, the % moisture, and the % ash are controlled in the machine direction (direction normal to the width of the paper and toward the reel) and for the basis weight, % moisture, and thickness, profile control in the machine cross direction (unevenness or flatness along the machine cross direction of the paper) is performed.

FIG. 6A is a schematic view of a basis weight sensor for measuring weight of a paper web W, which is installed in almost all of known quality control systems (referred to as QCS). In the basis weight sensor, a β-ray source (radioisotope) is used as a source. The weight of the paper web W is measured by measuring attenuation of β-rays due to absorption by the mass, performing comparison with a calibration curve that is calibrated in advance by using a standard sample, and performing backward calculation based on the ratio between the transmitted signal of the β-ray received at a receiver (ion chamber) and a signal when there is no paper web W.

The above-described attenuation of a β-ray can be represented as a basis weight attenuation curve according to Beer's law, as illustrated in FIG. 6B, and the following equation is established.

$$I = I_0 * e^{-\mu * t}$$

Equation 1

In Equation 1, I is a transmitted signal amount, $I_0$ is an incident signal amount, μ is an absorption coefficient, and t is mass (thickness).

Control of quality parameters based on these measured values is carried out by a device referred to as an actuator. Typically, in control in the machine direction, stock valve control is performed to adjust the concentration of the cellulose fiber input, and for controlling % moisture, vapor pressure control at a dryer is performed to adjust the drying state. In the machine cross direction, for controlling the basis weight, dilution water is used to adjust the concentration upon supply from the head box (for example, a dilution water actuator illustrated in FIG. 2), % moisture is controlled by re-wetting or re-moisturizing or drying by steam heating or drying by IR heater, and the thickness (caliper) is controlled so as to be a target value by heating or cooling calender rolls to change their diameter and thereby changing pressure at the calender.

FIG. 3 illustrates a sensor head of a scanner carrying out sampling measurements by scanning the surface of the paper web. In this sampling method by scanning, fluctuations in quality parameters due to millimeter size structural fluctuation factors in paper which is known as paper formation, fluctuation in measurement point of quality parameters due to randomly occurring washing shower problems in the machine cross direction, and web wander/web shrinkage, and fluctuations in quality parameters due to defects of equipment in the paper machine rotating at high speed, such as a wire, press roll, felt, canvas (not illustrated), and so on which have rotation cycles from several meters to several tens of meters are measured as noise (external disturbances). Such noise are removed by using a technique called filtering for smoothing out the measured values and a measured representative value is determined. The average measurement values of the paper over the whole width or the profile of the paper in the machine cross direction is represented using this processed data, a difference from the target control values is calculated, and the quality parameters are controlled and corrected using a device known as an actuator.

FIGS. 8A to 8C are a photograph of unevenness (weight variation) in paper, which is called formation and the most characteristic property of paper, and schematic diagrams of known moisture sensors. A sampling locus of a sensor running (scanning) on the paper web W is indicated by reference numeral 813, and here, one dot represents a spot having a diameter of 10 mmφ and measurement is performed every 1 msec. The formation refers to an uneven state formed by thickened parts due to high concentration of fibers, like a part indicated by reference numeral 801, and thinned parts, like a part indicated by reference numeral 802, which alternately exist. Some of the paper formation flock size is similar to the measurement sensor spot size. That's weight ratio may be a dozen percent, which may cause a fatal error in measurement at one of sampling points. Thus, in known moisture meters, an infinite random scattering method by using a scattering plate like reference numeral 807 in FIG. 8B or an integrating hemisphere type scattering method like reference numeral 810 in FIG. 8C are used.

Reference numerals 808 and 812 denote halogen lamps as light sources, and reference numerals 803, 804, 805 and 809 denote light receiving elements. In FIG. 8B, three wavelengths are measured simultaneously using a beam splitter 806 and a bandpass filter provided in front of the light receiving element. In FIG. 8C, a rotary filter 811 is rotated on the light source side and measures three wavelengths with one light receiving element. The difference between the two method is as follows. In the method of FIG. 8B, measurements for the same spot at the same time are performed, but minimization of difference in characteristic between the elements is required. On the other hand, in the method of FIG. 8C, measurements are not performed at the same time, but stability relating to the light receiving element can be ensured.

FIG. 4 illustrates a manner of appearance, on the paper web, of sudden changes and short period repeating fluctuation caused by paper machine equipment, which are removed from data during filtering when a scanning type sensor is used, and a manner of appearance of continuous fluctuation at cross direction fixed location, which remains in the filtered data. The dotted line represents a scan locus of the sensor head of the scanner, and in a high-speed machine (paper machine), such a scan locus per half cycle has a length of several hundred meters. Points a and c in FIG. 4 are points in the continuous fluctuation at cross direction fixed location that are always measured by the sensor (not illustrated) of the sensor head. Points b and d in FIG. 4 are in repeating fluctuation that always appears in the paper, but due to changes of measurement position of the sensor during the scanning, this fluctuation is removed as a result of filtering and thus is not measured. In addition, sudden changes are hardly detected by the sensor, and even if sudden changes are detected, they are filtered out as spike fluctuation, as in the case of repeating fluctuation. The continuous fluctuation at cross direction fixed location measured by the sensor also need to be filtered as described below, because measurement interval at an identical point varies, as illustrated in FIG. 3, and fluctuation in the machine direction is also included.

FIG. 5 illustrates step responses when filtering is performed using moving average and exponential filtering to suppress measured spike fluctuations to separately measure errors in the machine cross direction and the machine direction. Typically, exponential filtering is used, and a suppression value of 0.2 is often used. "SAMPLES" on the horizontal axis represent the number of scans (number of crossings), and one scan takes about 20 to 30 seconds. The step response is a response when measurement is performed without scanning. By observing the step response, it can be understood that about 10 scans (several minutes) are required to obtain a 90% response, and thus controllability is significantly lost. Also, even if high-speed errors caused by the machine equipment occur repeatedly, the chances of detection for such high-speed errors is 0.17% and thus they are filtered out as random noise and cannot be observed.

As described above, in the scanning method, it takes several tens of seconds or more for the sensor head to cross the width of the paper web, and the controllability including time required for filtering of measured values etc. may be several minutes to a dozen minutes. Therefore, errors caused by equipment rotating at high speed such as paper machine equipment cannot be measured.

In order to solve the above problem, as disclosed in PTL 2, attempts have been made to perform fiber measurement or % moisture measurement using an infrared camera, which can measure the entire width of the paper web at once, and without using scanning. In this infrared camera based system, an InGaAs infrared linear array (line sensor) is used and the same measurement principle as the scanning method is used. In other words, in this infrared camera based system, the weight of the paper web is determined using three wavelengths, which are a wavelength absorbed by water, a wavelength absorbed by cellulose fibers, and a comparative wavelength that is not absorbed by either water or cellulose fibers. Infrared light emitted from the light source (halogen lamp) passes through the paper web to be measured and then enters the infrared line camera. Here, a plurality of infrared line cameras is provided, and the infrared light is split by a beam splitter and then enters each of the cameras. This is a general method for eliminating errors depending on measurement points due to fiber aggregation distribution in the paper web, which is called formation, ranging from several millimeters to a dozen millimeters, and the weight ratio reaching several percent, and called measurement at the same point at the same time. This method is an appropriate method because the intent is to perform quick quality parameter control by high-speed measurement to improve paper quality and minimize energy loss in the manufacturing process.

CITATION LIST

Patent Literature

PTL 1: Japanese Unexamined Patent Application Publication No. 2004-277899
PTL 2: U.S. Pat. No. 6,355,931

SUMMARY OF INVENTION

Technical Problem

As described above, in the paper machine illustrated in FIG. 2 or disclosed in PTL 1, the measured values are obtained by scanning transversely at an incline the paper as it travels at high speed, so the measured values include both a component in the machine cross direction and a component in the machine direction (see FIGS. 3 and 4), and heavy filtration is applied to the measured values in order to separate the components (see FIG. 5). Therefore, this has the major problem that when the operator has adjusted the machine for control of the quality parameters, the result cannot be seen until after a wait of more than 10 minutes.

Also, the wound product (paper) can vary from several thousand meters to several tens of thousands of meters, from thick to thin, and typically it takes about one hour to produce one roll. At this time if the average measured values of the quality parameters of each wound roll are compared, it is found that the values are contained within a comparatively small tolerance range, and at a glance it appears that good measurement control is being carried out, but typically within the several tens of thousands meters in one wound roll variations ranging from ±1% to several percent are included, and at the level of the smaller units that the customer actually uses, for example photocopy paper, this cannot be said to be the result of good control. The result is sheet break and/or sheet jamming in printing machines or photocopy machines.

In addition, at present typically a Quality Control System (QCS) is used for measuring and controlling paper quality, and for measurement of basis weight (g/m), which is the basic parameter, a radiation source (β-ray) such as Kr85 or Pm147 is necessary, a permit must be obtained for their use, and radiation control personnel are required. Since beta rays are absorbed by all masses including air, correction is performed by calculating air layer weight by measuring the gap distance between the source and the receiver and the temperature of each zone of the air. As for the main measurement time, about 1 millisecond sampling is mainly used, and the measurement spot size is about 10 mmφ. A standard sample for correction for dirt deposited between the source and receiver during measurement is internally provided (see FIG. 6A), the sensor is periodically moved to an off-sheet position, the shutter is opened and closed to perform at least three point measurement including open count, closed count, and internal reference sample count for correcting deviation from the attenuation curve at the time of calibration. This is called standardization, and is performed once every tens of minutes. When a lot of dirt is generated, for example, in a case of a tissue, the standardization is performed frequently and it is necessary to take measures to prevent paper dust from entering the gap. Correction of the weight of the air is also a problem in known measurement devices. As described above, in measurement using a R-ray source, various corrections are necessary, and maintenance in order to maintain accuracy is a significant burden. Therefore, at present this kind of measurement control is still not carried out on the small paper machines of small and medium-sized companies. Also, for very thin tissue paper and also heavy board paper, because of limitations in correction for β-ray sources and the difficulty of determining water weight, so that sensors are used as condition monitoring, and it is still far from ideal aim of absolute paper property measurement control.

The currently used measurement methods as described above are all successive sampling measurements by sensors mounted on a scanner, and with this method machine direction and machine cross direction variances in the web are included in measured values. Also, even with a short measurement time of 1 millisecond, if for example it required 20 to 30 seconds to cross the web on a paper machine of 6 m width, for paper machines with speeds in excess of 1000 m per minute only 0.2% or less of the web would be measured.

By using the above-described filtering used to smoothing out external disturbances, short period external disturbances, in other words fluctuations due to the paper machine equipment, are filtered out and are not seen by the operator, and as a result if the comparatively long period winding level average values match the target values it is considered acceptable. This is producing a consistent finish while external actuators are forcibly applying load on the paper, but without understanding what is causing the error in measured values, and at certain times this can cause an external disturbance to another sensor, which has an adverse effect in terms of feedback control theory. This is inevitable in the current measurement technology because, even if the cause of the error is a fault in the paper machine equipment, in other words a washing shower problem, eccentricity of the roll, bias, and so on, such errors are filtered out and high-speed measurement for such errors is not available.

The method using an infrared camera described in PTL 2 employs a full-width measurement without scanning, which fundamentally changes the problem of measurement control by the methods using scanning. However, unlike scanning sensors, drawback of fixed sensors is that they essentially do not have capability of moving from online to offline (by being moved outside the paper web) for standardization for maintaining accuracy, and thus it is not possible to maintain accuracy. This method cannot be a direct substitute for the existing system, but if the accuracy of the sensor can be improved to resolve the problem of insufficiency in accuracy, which was a disadvantage, then this problem can be solved, and in addition, a great economic effect and improvements in quality and a shift in manufacturing technology and operation technology can be achieved.

An object of the present invention is to provide, by improving the method using an infrared camera disclosed in PTL 2, a quality measurement method and a quality measurement device for a long sheet material that does not carry out the scanning type successive sampling as used in known systems, that measures quality parameters of paper separately in the machine direction and the machine cross direction, that does not require radioactive rays (β-rays) and X-rays conventionally used, that does not carry out scanning or filtering, that can be applied even to small paper machines, that can achieve improved accuracy, and that has high economic effect.

In addition, an object of the present invention is to provide a novel quality measurement method using optical measurement and a method for improving current control methods that can be achieved because it does not use scanning, by considering the ash sensor, that measures ash components (titanium oxide, calcium carbonate, clay, etc.) currently used to prevent characters on the opposite side of the paper from being see-through, as a light strike-through sensor, which is an original purpose.

Solution to Problem

A quality measurement method for a long sheet material according to the present invention is a method in which an infrared LED light source that emits light having a wavelength necessary for measuring paper quality is provided on the opposite side of the long sheet material to an infrared camera, an amount of transmitted light attenuated due to absorption by a measurement target included in the long sheet material and described below and an amount of comparative transmitted light having a similar wavelength that is not absorbed by the target are measured, and the weight of the target is determined based on a measurement equation obtained by performing calibration in advance. Examples of the measurement target include cellulose, filler and water, which are main components of paper, as well as substances to be coated such as resin, binder, and silicon which are typically measured by an infrared absorption method.

The present invention can be applied to measurement of a plastic film such as a PP (polypropylene) film, a PE (polyethylene) film, or a PET (polyester) film and a coating agent.

In the present invention, an InGaAs area sensor is used in an infrared camera serving as a light receiving unit, and depending on a required number of channels, infrared LED light sources corresponding to respective absorption wavelength bands are provided as light sources (for example, see FIG. 7B). For example, for moisture and fiber measurement, 1.45 μm, 1.57 μm, and 1.3 μm light sources, as described in PTL 2, are arranged in the machine direction so as to be spaced from each other so that they are not affected on the paper web (so that they do not interfere with each other). As a result, measurement at the same point at the same time can be achieved by performing offset measurement, and in addition if sufficient averaging is performed in consideration of formation distribution in the paper web, removal of fine noise that cannot be achieved with the current sampling method can be achieved.

In the quality measurement method for a long sheet material according to the present invention, for example, for % moisture measurement for a thick paperboard or for measurement of the amount of coating on the surface, the infrared camera and the infrared light source may be provided on the same side of the long sheet material and an amount of reflected light may be measured instead of the amount of the transmitted light (see, for example, FIGS. 12A and 12B). Although this method cannot be used for measurement of fibers that are most predominant component of the entire web, for example, % moisture or the thickness/weight of a coating layer with the fibers is measured based on attenuation of absorption wavelength with respect to a comparative wavelength. The measurement is based on the same principle as reflection type moisture meter, which is the prior art, but the infrared area sensor and the infrared LED are used and scanning is not performed.

The infrared camera in which an area sensor is used and the light source which is an infrared LED for each wavelength are described above, and here, how to use the infrared LED light source will be described. In the method using the line sensor disclosed in PTL 2, a camera focused on the surface of a paper web measures transmitted light which has been scattered, absorbed, and reflected in the web. Light entering the camera from the surface, as viewed from the camera, has been attenuated by the fiber weight and the water weight of the paper web, and the attenuation is subject to Beer's law (Equation 1). The line sensor is provided so that the measurement point of the line sensor is located almost at the center of a light band on the web. The width of the band of light emitted to the paper must be designed, depending on the size of the line sensor device, so that the measurement point does not deviate from the band due to the effect of fluttering or the like (waviness of the paper web to be wound). In the case of the transmission type, if the light source and the light receiving unit are normally provided with respect to the plane of the paper, difference is only in the distance. However, in the case of the refection type, the plane of observation is changed due to fluttering because they cannot be placed on the same perpendicular line. On the other hand, since the area sensor picks up all the transmitted light, such an effect is minimized. For example, when the size of the light source is 20 mm$\varphi$, the size of a receiving surface at the area sensor is designed to be 50 mm$\varphi$ or more.

The positional relationship between the light source and the light receiving unit (camera) according to the present invention is as described above, and next, the arrangement of the LED bulb of the light source and the method of irradiation will be described. In usage as an LED light source (1), by using an LED bulb with a lens directly attached thereto or by providing a cylindrical lens above a shell type LED bulb, light is caused to converge so that sufficient luminous flux can be achieved at the measurement surface. This works like a β-ray beam emitted from a radiation source in a typical basis weight sensor, and similarly to the ion chamber, the area sensor picks up all the transmitted light that has passed through the paper web. Conceptually, this case is analogous to a situation in which a large number of basis weight sensors or infrared weight sensors are arranged throughout the surface of the paper web.

Usage as an LED light source (2) is a method in which light converged in the machine direction by using a cylindrical lens is diffused only in the machine cross direction by using a special film. In this method, a pseudo single band of light is formed, and division in the machine cross direction (measured value is taken for each separated section) is performed by dividing any range in the field of view of the camera using software (see FIGS. 10A to 10C and 10A' to 10C'). The advantage of this type of light source is that the boundaries between the LED bulbs are eliminated, and the accuracy of measurement for the shrinkage rate of the paper web, which will be described below, etc. increases. Practically, a 10 mm to 20 mm linear light source is used, and mini slices in which the minimum slice (division width) is set to 10 mm or slices that are adapted for the control actuator, for example, 65 mm slices are used.

In the quality measurement method for a long sheet material according to the present invention, an infrared camera (generally an infrared camera for a near infrared wavelength band using InGaAs, but other devices may be used) and an infrared LED light source are used, an area sensor is used as a light receiving unit and a narrow-band LED light source that emits light absorbed by the measurement target is provided as a light emitting unit, the total number of captured photons is measured without using a bandpass filter, or the like on the light receiving element side, and conversion into weight is performed by using an equation calibrated in advance. Although the same principle as a typical infrared moisture meter or basis weight sensor using a scanning-based sampling method is used, the quality measurement method for a long sheet material according to the present invention is significantly different in that offline measurement and calibration are performed for each slice (or for each LED bulb) using a standard sample over the entire width. Naturally, there is variation in the emission intensity of the infrared LED and the characteristics of each pixel of the light receiving element, so a measurement calculation formula for each measurement range is required. In the calibration, by performing dark current measurement on the camera side or maximum intensity measurement using a pseudo sample that does not exhibit absorbent property, such as synthetic paper or aramid paper in which light is scattered but is not absorbed by cellulose, a standard sample can be obtained. This corresponds to the shutter open state (open count) and the shutter closed state (closed count) of the radiation source in the basis weight sensor described above. These are reference values (time zero count) in the offline state. In addition, calibration is carried out, as in the existing system, by providing a real web sample prepared for each required paper grade, on the actual pass line of the paper web, performing thorough scanning to obtain a sufficient average value, and measuring a signal of each infrared channel, which is equivalent to the number of photons. If the irradiation area has an area of a 10 mm$^2$ and measurement area per pixel is 1 mm$^2$, then there are 100 pixels. Here, each pixel can have 1024 or more step gradation, and thus the total number of counts can range from 0 to 102,400, which means better resolution compared to 13-bit ADC.

From the relationship between the camera (light receiving element), sample (paper web), and infrared LED (light emitting element) at the time of calibration at time zero, the calculation formula for measurement, for backward calculation for determining the fiber weight, water weight, etc. in the paper web can be obtained. At the same time, by finding differences in balance with respect to time zero, light source errors, camera element errors, and other online errors (errors caused by the paper machine in operation), etc. are found, and errors to be corrected online, for example, light attenuation due to dirt on the entire light source are distinguished from partial attenuation, due to failure of each LED and camera, etc.

The calibration is performed throughout the entire width by using a slice width determined according to the purpose, for each of the standard sample (pseudo paper sample that does not exhibit absorption at any wavelength) and the real web sample of each paper grade actually manufactured (fiber weight, water weight and % ash). It is important to use an apparatus for scanning and measuring the sample over the entire width and a method of thorough averaging that is not affected by the formation. An apparatus for this calibration is not illustrated in the figures, but is an apparatus that scans and measures a pass line through which a paper web passes, over the entire width, and has a function of cleaning the light source at the time of a reel change when it is online. Sample holders are placed at both outsides of the sheet but on the same level of pass line so that the real web sample and the standard sample can be measured online.

For calibrated data of each slice (for example, every 10 mm), the amount of light transmitted through the paper web and emitted from the surface is measured, and the distance from the light receiving element is normalized (in the calculation, a median value of 1 is used, and it is assumed that there is inversely proportional relationship with respect to the square of the distance), and conversion is performed. Since the weight of the sample is known, data for several sheets in which a target value for each paper grade is interposed are taken and applied to the equation, and converted into a weight to be obtained according to Beer's law. This calibration method is not different from those for the existing systems, but care must be taken in differences in distance due to the field of view of the camera, differences in the characteristics of each pixel of the light receiving element, differences in the % ash, sample handling and the like.

An important point of the present invention is that calibration is performed by including various elements such as sensitivity of each pixel of an InGaAs area sensor that is an element inside the camera, device size difference, LED intensity difference between the light emitting units, and wavelength band pattern difference (for example, half width). In a determined slice width, it is premised that these differences have repeatability. Since the measured value shift of the whole camera (fluctuation in dark current value), light attenuation due to dust on the light source, and the fluctuation of the amount of light due to the fluctuation in the power source for the light source, etc. which is appeared in the entire camera or the entire system and is not appeared slice by slice, and thus they can be corrected or corrected as an alarm, or excluded from the measurement target as an abnormality.

Another important point is online automatic standardization or grasping of the condition of the sensor equivalent to the online automatic standardization, and making corrections as necessary. In known scanning sensors, the sensor head is moved to the offline position at fixed time intervals, open count, closed count, and standard sample measurement as described above are performed, and difference from time zero in measurement between the light emitting side and light receiving side of the sensor is standardized. The measurement difference is caused by various factors such as dirt adhesion between the source and receiver, change over time of the light source on the source side, and change of the gap due to ambient temperature and thermal strain, therefore the standardization of the measurement difference is necessary for maintaining sensor accuracy and performed every tens of minutes. In a process in which a lot of dirt is generated, for example, a tissue machine, the standardization of the measurement difference needs to be performed frequently and as a result, measurement ratio will further drop despite it is already small.

For the system using a line sensor disclosed in PTL 2, there is no description about such automatic standardization, and it is believed that the accuracy cannot be maintained in practice. In a sense, among the elements mentioned above, the use of a halogen lamp as a light source is fatally problematic. The lifetime of halogen lamps is 2 to 3 months, and paper machines usually are not shut down for several weeks, and thus difference compared to the calibration at time zero becomes quite large. The reason why the present invention uses an infrared LED as a light source is that the lifetime of infrared LED is as long as several years and exhibits a stable repeatability because it is a semiconductor device. Since there is no opportunity of offline, what is required for full width measurement using a camera is a method of condition check between the camera and the light source equivalent to the automatic standardization.

An improvement in the present invention over the prior art is achievement of stability and long life of the light source by using an infrared LED, and a solution of problem on the light source side for which automatic standardization is required. Furthermore, it is possible to check the conditions of the source (light source) and the receiver (camera) based on comparison between the measured values in an overlap area between adjacent cameras, and as for dirt and other online effects, a necessary correction coefficient can be obtained by measuring and comparing the real sample and the standard sample in a field of view outside the sheet. As a result, it is possible to know the change with respect to time zero based on the automatic standardization without moving the camera and the light source to the offline position.

Advantageous Effects of Invention

A quality measurement method for a long sheet material according to the present invention is a quality parameter measurement method for a long sheet material in which a quality parameter of the long sheet material moving toward a winder is measured by using an infrared light source configured to irradiate the long sheet material and an infrared camera configured to receive infrared traveling via the long sheet material. The method includes, performing simultaneous measurement for the entire width of the long sheet material by using the infrared light source and the infrared camera, performing online grasping of conditions of the infrared light source and the infrared camera, and performing online correction of a measured value based on the conditions. Here, the term "infrared" includes "near infrared". In addition, "traveling via" refers to transmission or reflection, and includes scattering and reflection inside the long sheet material during transmission.

According to the quality parameter measurement method, since the entire width of a long sheet material wound at a paper machine or the like is simultaneously measured, the quality parameter can be measured almost throughout the long sheet material, and thus the cause of fluctuation in the quality parameter can be easily determined. To cover the entire width of the long sheet material, a plurality of infrared light sources and infrared cameras may be arranged in the machine cross direction. In the obtained measured value, the fluctuation in the machine direction and the fluctuation in the machine cross direction are separated from each other, and thus it is not necessary to perform the filtering. As a result, the cause of the fluctuation in the quality parameter may be quickly and appropriately eliminated. Furthermore, since the condition of the infrared light source and the infrared camera are grasped online and the measured values are corrected online based on the condition, the accuracy of the measured values is improved, and as a result, the quality of the long sheet material is improved.

The quality parameter measurement method for a long sheet material according to the present invention may further include preparing a plurality of the infrared cameras to be arranged in the machine cross direction of the long sheet material so that fields of view of adjacent infrared cameras overlap each other, acquiring difference between measured values for an identical point on the long sheet material, that measured by using the adjacent infrared cameras, respectively, and adding the difference to the measured value from each of the cameras.

With the measurement method, the consistency of the measured values measured by the plurality of cameras used to measure the entire width simultaneously can be checked by comparing the measured values for the overlap areas where the fields of view of adjacent infrared cameras overlap. Since the difference is added to the measured value of the camera for which difference has been found based on the comparison result, the measurement accuracy for the quality parameter can be maintained even when the measurement is performed by using the plurality of cameras. Also, when 60% of the field of view of each camera is overlapped, even if one of the cameras fails, backup can be performed by using an adjacent camera.

The quality parameter measurement method for a long sheet material according to the present invention may further include preparing a reference sample to be placed near the long sheet material, and irradiating the long sheet material and the reference sample with infrared from the same infrared light source, and simultaneously measuring, by using the same infrared camera, infrared traveling via the long sheet material and infrared traveling via the reference sample, to perform standardization and correction of the measured value acquired in the simultaneous measurement for the entire width of the long sheet material. Here, the term "standardization" refers to comparing the measured value of the reference sample with the measured value of the paper web to obtain a difference, and the term "correction" refers to adding the difference to the measured value for the paper web. The reference samples include, in addition to a real web sample of each paper grade actually manufactured, a standard sample prepared by using, for example, pseudo paper that does not absorb the absorption wavelength of water or pseudo paper that does not absorb any wavelength.

In this measurement method, the real web sample and the standard sample are measured with the same camera at the same time as the long sheet material in a field of view outside the long sheet material, and by comparing the measured values, a necessary correction coefficient can be obtained. This can ensure the consistency among the plurality of cameras arranged across the entire width of the paper web, as described above, and by measuring the quality parameters of the reference sample simultaneously with measuring of the quality parameters of the long sheet material, it is possible to check the conditions of the light source and the camera online (i.e., without stopping the paper machine) and, based on the results of the check, perform standardization and correction of the measured value. Therefore, it is possible to remove fluctuation in the measured value due to causes other than fluctuation in the quality parameter, and thus improvement of the quality of the product can be achieved.

In the quality parameter measurement method for a long sheet material according to the present invention, an infrared area camera may be used as the infrared camera. Since the field of view of the infrared camera covers an area instead of a line, even if a change in the observation surface occurs due to fluttering of the long sheet material, all transmitted and reflected infrared light can be picked up.

The quality parameter measurement method for a long sheet material according to the present invention may further include preparing a plurality of infrared light sources, each configured to emit infrared having a different wavelength, to be arranged in the machine direction of the long sheet material, and measuring simultaneously, by using the same infrared camera, rays of the infrared traveling via the long sheet material. Infrared light sources for different wavelengths are spaced at minimum intervals (for example, 50 mm intervals) so that their irradiation areas do not interfere with each other.

With this measurement method, by setting appropriately the number of channels and wavelengths required for the measurement, and by performing the offset measurement, a plurality of quality parameter can be measured at the same point at the same time (for example, absorption wavelength of fibers, wavelength that is not absorbed, absorption wavelength of water, a comparative wavelength from reflection direction, etc.).

The quality parameter measurement method for a long sheet material according to the present invention may further include, receiving, by the infrared camera, transmitted infrared and reflected infrared emitted from the infrared light source and traveling via the long sheet material, and measuring a light scattering ratio of the long sheet material, based on transmittance calculated based on the received transmitted infrared intensity and the received reflected infrared intensity. The "light scattering ratio" refers to a "light strike-through degree" which indicates a quality of paper related to light transmittance.

With this measurement method, the light scattering ratio can be measured only by using the light source and the camera used for measuring other quality parameters and without performing measurement of ash weight which has been conventionally performed. There is no need to prepare additional measuring equipment, and there is no need to use radioactive rays (basis weight sensor) and X-rays (ash weight meter) that has been conventionally used.

A quality control method for a long sheet material according to the present invention includes, determining, based on the light scattering ratio acquired by using the measurement method described above, whether attenuation in the transmitted infrared intensity is caused by fibers or ash, to perform determination for correction of quality parameters, including fiber weight and water weight, relating to light path length or determination for process condition change. The "light path length" refers to the length of a path infrared scattered and reflected inside the long sheet material takes. "Process condition change" includes a change in control of thickness, etc., in addition to the quality parameter control described above.

With this control method, it is possible to achieve things that could not be determined in conventional ash weight measurement, and thus improvement of the quality of the product can be achieved.

A quality control method for a long sheet material according to the present invention includes, synchronously with a reel change for a wound roll in the winder, measuring quality parameters, including fiber weight and water weight, by using the measurement method described above, while changing the quality parameters at a predetermined cross direction control point and by a predetermined amount, and based on the measured value acquired, checking positional relationship between a measurement point and the cross direction control point for basis weight control or water weight control, which has changed due to shrinkage or wander in the machine cross direction of the long sheet material being wound. This is a so-called bump test (output response test).

With this quality control method, the quality parameter can be measured in a short time, and thus in the short time for the reel change, it is possible to change shrinkage pattern in the machine cross direction for each reel change without generating waste paper due to use of paper which is not essentially offered for sale. Since it is possible to correctly determine position of slice in the head box at which the basis weight and the water weight should be controlled, it is possible to prevent error diffusion in the machine cross direction.

A quality parameter measurement device for a long sheet material according to the present invention is a quality parameter measurement device for a long sheet material that measures, by using an infrared light source and an infrared camera configured to receive infrared, a quality parameter of the long sheet material moving toward a winder. In the quality parameter measurement device for a long sheet material, a plurality of the infrared light sources and a plurality of the infrared cameras are arranged in the machine cross direction so as to cover the entire width of the long sheet material, and fields of view of adjacent infrared cameras overlap each other.

With this measurement device, even when a plurality of cameras is required because scanning is not employed, the above-described quality measurement method for obtaining a highly accurate measured value can be performed.

The quality parameter measurement device for along sheet material according to the present invention may include a reference sample. In the quality parameter measurement device for a long sheet material, the reference sample may be placed in an extension plane of the long sheet material in the machine cross direction so that the reference sample and the long sheet material are irradiated with infrared from the same infrared light source and so that infrared traveling via the reference sample and infrared traveling via the long sheet material are measured simultaneously at the same infrared camera. The reference sample may be fixed at the above-described position, or a plurality of reference samples may be rotated to come to the above-described position.

With this measurement device, the above-described measurement method for obtaining a highly accurate measured value by performing standardization and correction of the measured value can be implemented.

In the quality parameter measurement device for a long sheet material according to the present invention, the infrared camera may be an infrared area camera, a plurality of the infrared light sources, each configured to emit infrared having a different wavelength, may be arranged in the machine direction, and the plurality of infrared light sources may be arranged so that infrared emitted from each of the plurality of infrared light sources and traveling via the long sheet material is measured simultaneously at the same infrared area camera, and so that irradiation areas of the plurality of infrared light sources do not overlap each other.

With this measurement device, all transmitted and reflected infrared can be received by the camera, and by the offset measurement, a plurality of infrared rays having different wavelengths provided according to the need can be measured at the same point at the same time.

As described above, the main points of the invention are (1) improvement of light source, (2) improvement by replacing line sensor with area sensor, (3) consistency check of overlap area, (4) online standardization and correction by checking standard sample and real web sample at off-sheet position, and (5) additional improvements relating to measurement control due to simultaneous measurement for entire width of a long sheet material.

With the quality measurement method for a long sheet material according to the present invention, a) by quality measurement for such as fiber weight and water weight of paper, that does not use scanning and does not use filtering, it is possible to confirm the high-speed fluctuations caused by paper machine equipment, that were hardly found by using conventional measurement methods, and thus improved controllability and control of elimination of causes of problems can be achieved. b) As a result, productivity is improved, and energy and labor savings are achieved. c) The present invention can replace a β-ray basis weight sensor and X-ray % ash sensor, and can be introduced in fields of thin paper such as tissue and toilet paper, where such measurement control was difficult, and thus operation management in manufacturing sites would be changed from sensuous operation to well managed operation. The present invention allows for d) transition from % ash sensor to light scattering sensor, as a new indicator, e) online paper web shrinkage measurement utilizing full width simultaneous measurement (100% measurement), and f) display of condition changes of equipment such as a color map of absorption wavelength of water, and thus allows for grasping of subtle machine state changes that was not available in conventional operations.

The measurement according to the present method and new control strategy based thereon can be introduced to more than 80% of the existing measurement control system market covered by the conventional QCS. And small-scale processes that have no experience of using QCS because of a difficulty to use a radiation source by the reason of both economic and technical also can introduce. The present invention can bring significant economic benefits to the whole industry, reduce energy consumption, reduce raw materials, and improve quality, and do not use radioactive rays and other hazardous materials. Thus, the present invention can make a great contribution to, for example, emerging nations in which production of packaging paperboards, sanitary paper, and the like continues to increase.

BRIEF DESCRIPTION OF DRAWINGS

FIG. 6B is a graph showing a basis weight attenuation curve according to Beer's law.

FIGS. 7A and 7B are a schematic diagram of a sensor using near infrared rays applied in the present invention. FIG. 7A illustrates a sensor 700 in which a light source 705 for one channel is provided, and FIG. 7B illustrates a sensor 710 including light sources 715 for three channels arranged in the machine direction.

FIG. 9 is a diagram illustrating a locus of a measurement area when measurement for the paper web W is performed by using an infrared camera.

FIGS. 10A to 10C and 1A' to 10C' are diagrams illustrating a structure for producing a linear light source using infrared LED light sources which are point light sources. FIGS. 10A and 10A' are a side view and a plan view of a linear light source 1002, FIGS. 10B and 10B' are a side view and a plan view of a set of point light sources 1003 converged in the machine direction, and FIGS. 10C and 10C' are a side view and a plan view of a set of point light sources 1005 spaced at regular intervals in the machine cross direction.

FIG. 11A is a schematic diagram of a quality measurement device 1100 according to an embodiment of the invention, FIG. 11B is a side view of a light source 1112, when 3 channel wavelengths are used, and FIG. 11C is a side view of a light source 1113 when one channel wavelength is used.

FIG. 12A is a schematic diagram illustrating a quality measurement device 1200 according to another embodiment of the present invention, and FIG. 12B is a side view of the quality measurement device 1200.

FIGS. 13A to 13C are schematic diagrams relating to measured values in an overlap area of fields of view of cameras. FIG. 13A is a top view of a light source 1320 and the paper web W, FIG. 13B is a graph showing measured values 1308 and 1309, and FIG. 13C is a graph showing measured values 1305 and 1306 at the time of calibration and normalized values 1307 and 1308.

FIGS. 14A and 14B are diagrams illustrating check of measured values by using a reference sample. FIG. 14A is a plan view of a paper web W and samples 1401 and 1402, and FIG. 14B is a graph showing a measured value 1405.

FIG. 15 is a schematic diagram illustrating a quality measurement device 1500 according to another embodiment of the present invention.

FIGS. 16A and 16B are schematic diagrams illustrating a quality measurement device 1600 according to another embodiment of the present invention.

FIG. 17A is a schematic diagram of measurement for a paper web 1706 with low % ash, and FIG. 17B is a schematic diagram of measurement for a paper web 1716 with high % ash.

DESCRIPTION OF EMBODIMENTS

Figure 1:
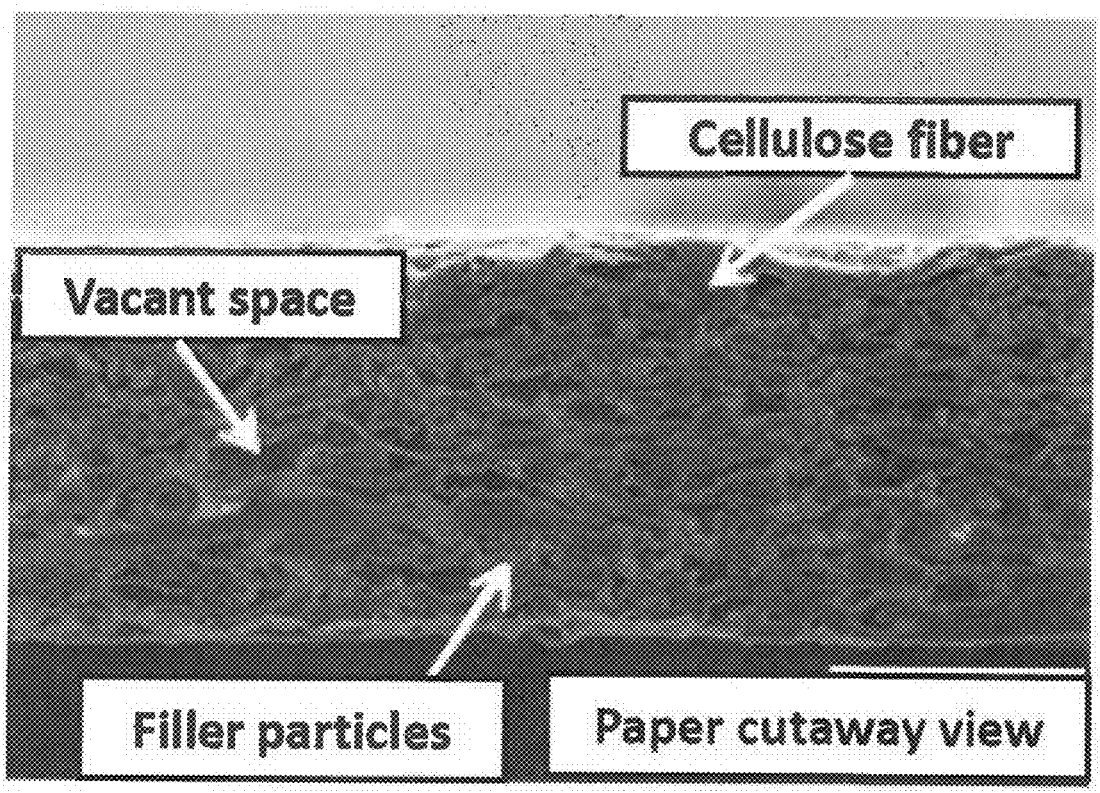
FIG. 1 shows a cross-sectional structure of paper which is most difficult to be manufactured among long sheet materials to which the present invention is applied.

Hereinafter, an embodiment of a non-scanning measurement method using an infrared camera of the present invention, for measuring quality parameters of a long sheet material, will be described in detail with reference to the drawings. Note that in the drawings, the same elements are given the same reference sign, and parts that are not related to the present invention have been omitted.

Figure 2:
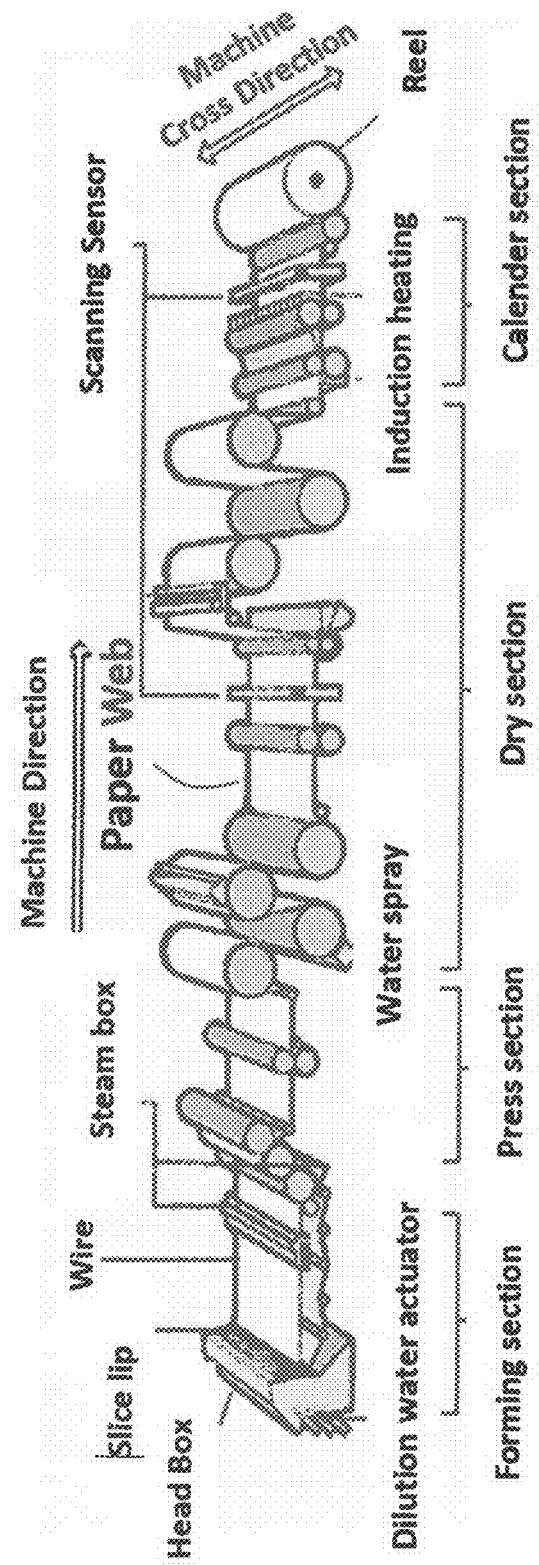
FIG. 2 is a schematic view of a typical paper machine including a known scanning sensor.
Figure 3:
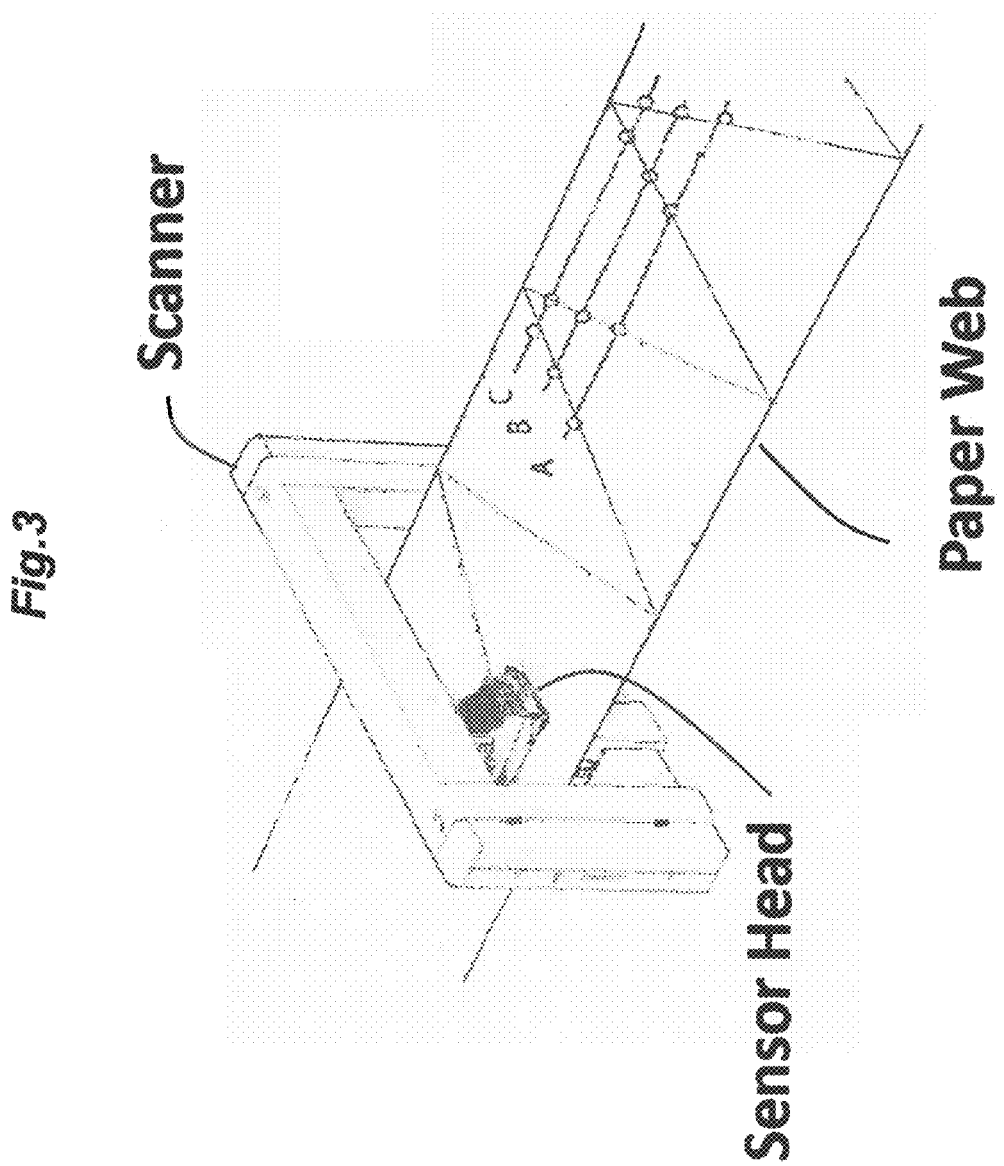
FIG. 3 is a schematic diagram of measurement using scanning in a known quality control system. (Source: Paper Machine Quality Control Systems (QCS) published by TAPPI Press)
Figure 4:
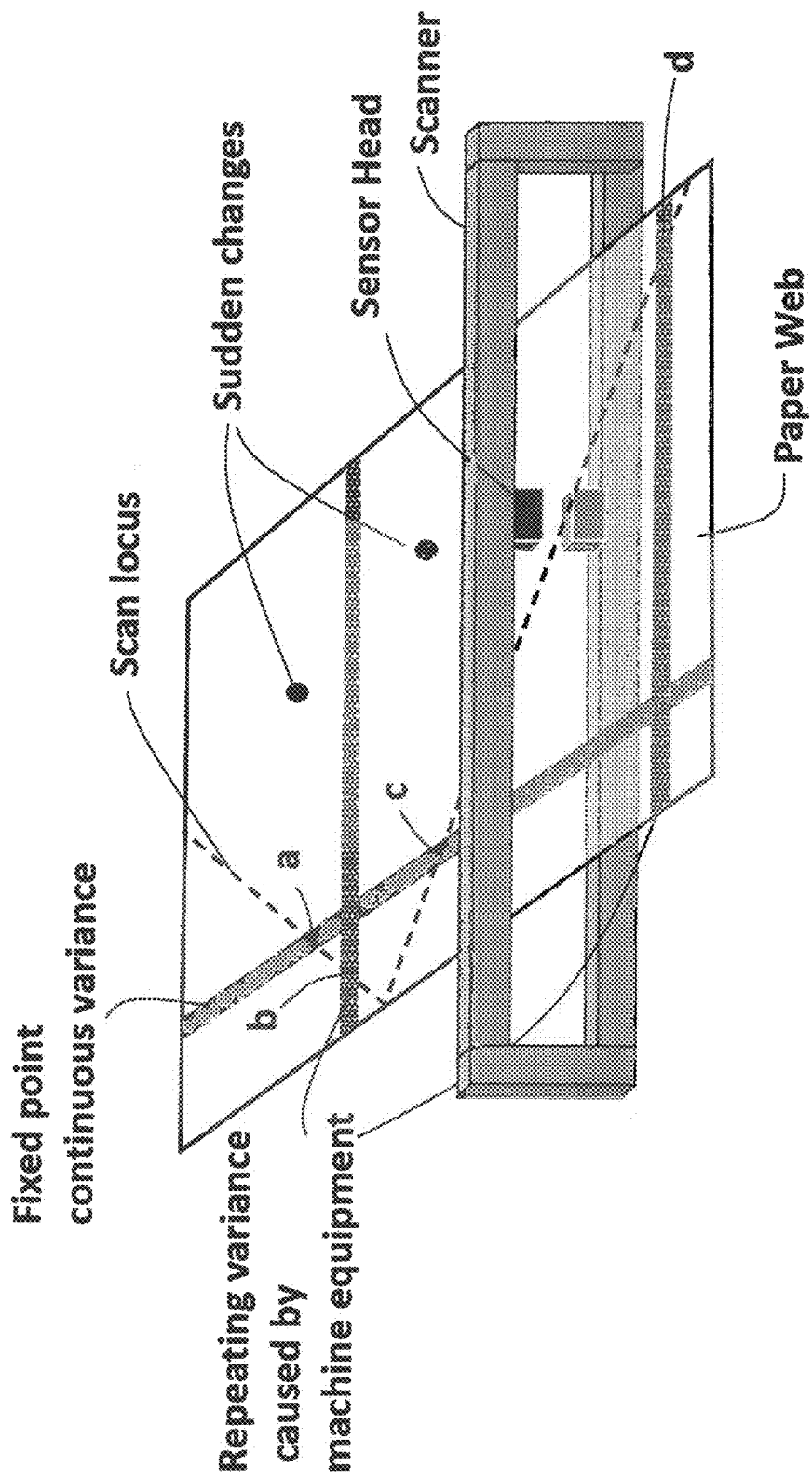
FIG. 4 is a diagram illustrating an example of fluctuations that can be measured and fluctuations that cannot be measured by a known scanning-type sensor.
Figure 5:
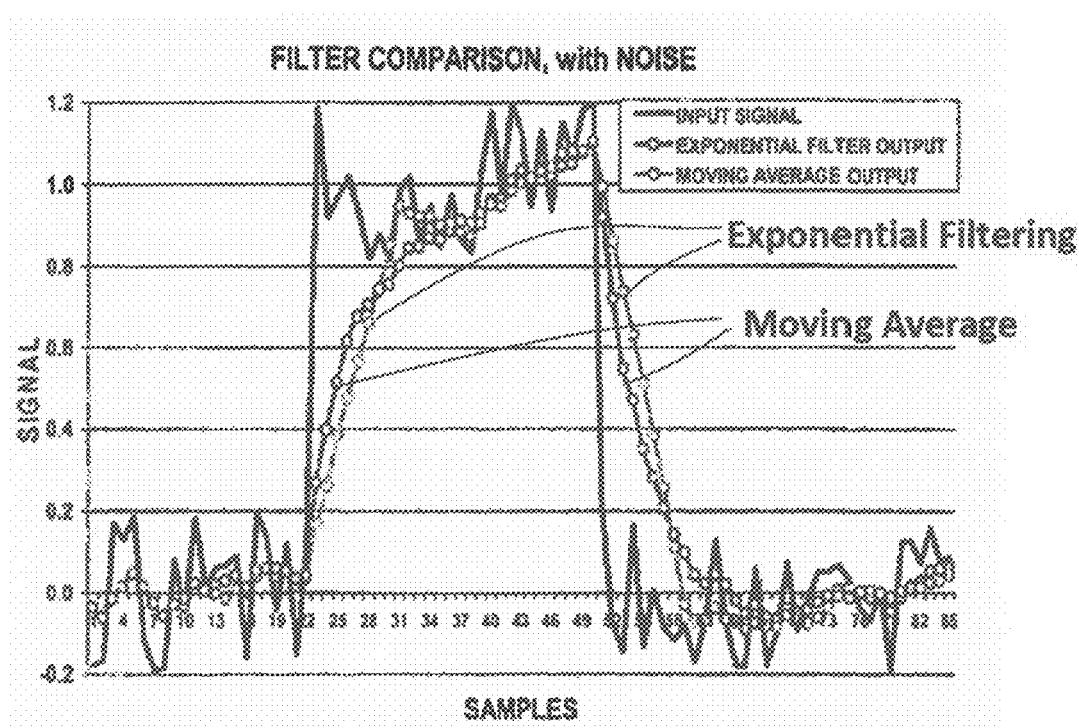
FIG. 5 is a graph showing measurement responsiveness as a result of filtering. (Same source as above)
Figure 6A:
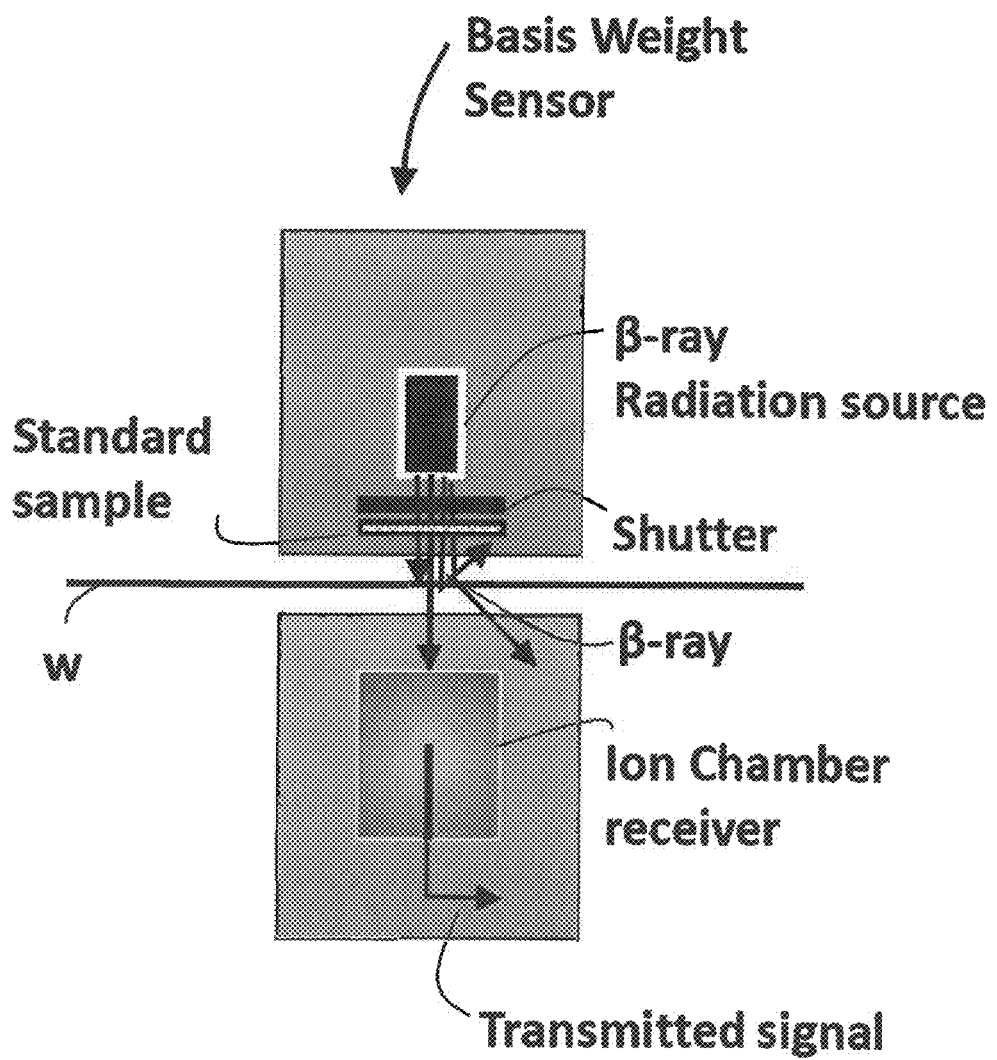
FIG. 6A is a structural diagram of a known paper weight sensor using an O-ray source (referred to as a basis weight sensor)

First, a paper web is described as a representative in a manufacturing process of a long sheet material to which the measurement method of the present invention is applied. FIG. 2 is a schematic diagram of a typical paper machine. It is believed that general configuration of the device at measurement point and concept of the measurement are common to cases of plastic films, nonwoven fabrics, and the like. For films, similar measurement technology can be provided, for example, when only a single substance such as PP, PET, or PE is used as the raw material, and when silicon or another material are mixed or coatings are made, and thus an embodiment of the present invention will be described for a paper web containing moisture that is a troublesome substance because it evaporates during the manufacturing process.

FIG. 1 is a cutaway view of a paper web to be measured by using the present invention. The paper web is composed of cellulose fibers as a main component, filler particles for scattering light, coloring the paper web, bonding, etc., contained water and many vacant spaces. When an additional coating process is performed, a chemical substance that improves printability is coated on the surface of the paper web together with calcium carbonate, clay, talc, or the like. In some cases, starch coating for increasing the surface strength is included in the papermaking process as a base sheet.

FIG. 2 illustrates a typical configuration of a paper machine. A quality measurement device according to the invention is disposed in, for example, a dry section or a calender section of the paper machine (for example, at a position of a scanning sensor in the figure). At the most-upstream side, a device called a head box is provided. The head box includes actuators for dilution water each provided for one of slice zones (divisions in the machine cross direction) and is configured to distribute the raw material in the machine cross direction so that the raw material is supplied evenly. The raw material to be supplied having a concentration of about 0.5% is contained in the head box. This state of the raw material is called a slurry (turbid liquid), and the slurry is supplied from a head box onto a wire. The supplied slurry is dewatered on the wire rotating at constant speed until 30 to 40% of moisture is removed, and as a result a paper web is formed. This section is called a forming section. Next, by sandwiching the paper web between a press roll and felt, a substantial amount of the water is squeezed out of the paper web. This is called a press section. Thereafter, the paper web enters a drying step (dry section) in which % moisture of the paper web is controlled to be about 5%, which is a target moisture value. The paper web passes through a calender section before the web is wounded. In the calender section, the surface of the paper web may be smoothed and, in addition, in some cases, the paper web is pressed to control the thickness thereof. Each section has an actuator for controlling the quality in the machine cross direction, and control of the concentration performed in units of slices by using dilution water, water profile control using water spray and steam heating, thickness profile control by heating the calender roll, etc. are performed. It is noted that, as control in the machine direction, overall concentration control for the slurry and temperature control in the dry section are performed to control the basis weight and the water content.

Figure 7A:
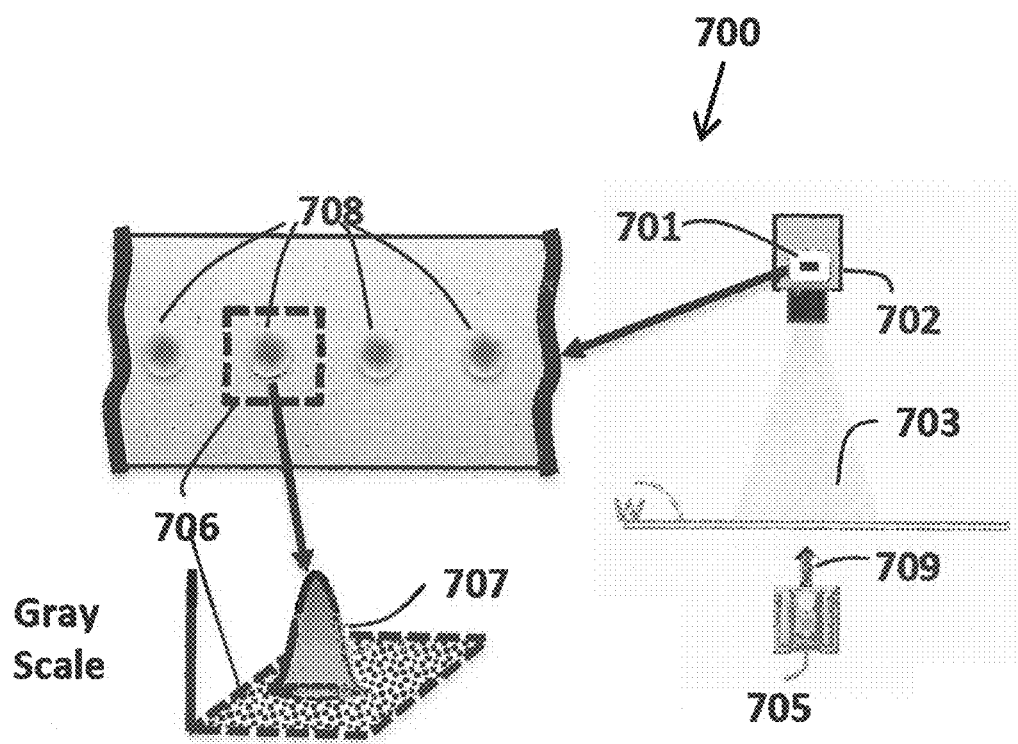

FIG. 7A is a schematic diagram of a non-scanning sensor 700 using an infrared camera to be applied to a quality parameter measurement device 1100 (see FIG. 11A) according to the present invention. In comparison with the above-mentioned concept of the known basis weight sensor, like an ion chamber, an infrared camera 702 includes an InGaAs area sensor 701 which is a light receiving element for capturing infrared transmitted through the paper web W. The infrared camera 702 receives transmitted infrared and measures total amount of the infrared. The light source is the infrared LED light source 705 selected based on an absorption wavelength and having a half width of about 50 nanometers. The infrared LED light source 705 is a semiconductor element expected to stably emit near-infrared light 709, like R-ray from Kr85 or Pm245, which is a β-ray source. The light output will drop to about 70% in several years, but is not unstable enough to, for example, require recalibration once a month when the machine is shut down. In PTL 2, a halogen lamp having a short life of about three months is used, and this is presumably a reason why high accuracy could not be maintained. In addition, the development of infrared cameras and near-infrared light emitting LED elements has been progressing, and they have been generalized so as to achieve economic sufficient effects in terms of price. The present invention presupposes a measurement method and a measurement device achieved by reviewing the InGaAs infrared camera and light source of PTL 2 which are problematic in terms of price and technology. Therefore, details thereof will be described.

In FIG. 7A, the infrared LED light source 705 and a field of view 703 of the camera for measuring the paper web W are illustrated. A single or a plurality of Infrared rays 709 for irradiation are provided depending on a substance to be measured. In the device according to the present invention, for example, as used in the prior arts or known scanning sensors, the wavelength of 1.57 m, 1.73 µm, or 2.1 µm may be selected as the absorption wavelength of cellulose fiber, the wavelength of 1.45 µm or 1.94 µm may be selected as the absorption wavelength of water, and a wavelength near these wavelengths may be selected as a comparative wavelength, that is not absorbed. Films and surface coating agents have different characteristic absorption wavelength bands, and thus selection of the light emitting LED and the number of channels are performed depending on target process. FIG. 7B illustrates a 3-channel measuring sensor 710 for the paper web. Similarly to the sensor 700, an infrared camera 712 includes an InGaAs area sensor 711 that is a light receiving element for capturing infrared 719 emitted from the light source 715 and transmitted through the paper web W. Reference numeral 717 denotes a field of view in the machine direction for the field of view 713 of the infrared camera 712, and a plurality of channels (three channels in FIG. 7B) of infrared light sources 715 can be arranged within the width of the field of view 717. The light sources 715 are offset from each other in the machine direction so that measurement areas of the light sources 715 do not overlap each other.

The principle of measurement will be described using FIG. 7A. When the light source 705 has an LED bulb with a lens attached thereto, the near-infrared ray 709 emitted by the light source 705 and transmitted through the paper web W is observed as a spot, like 708, as a result of attenuation due to the transmission. The area sensor 701, that is a light receiving unit, measures total amount of light for the spot by using image processing. Conceptually, when, for example, 4096-step (10-bit) gradation is used and the vertical axis represents a gray scale having 4096 steps, for an InGaAs element divided in the machine cross direction and the machine direction, as illustrated as 706, the total amount of light is determined by measuring a volume of an image 707 representing, in the 4096-step gray scale, signal amounts from each element in an area defined in advance so as to sufficiently include the entire irradiation area. Background (dark current signal amount), when the light source is turned off, for the same measurement area is periodically measured, and from the measured total signal amount, a total of the measured backgrounds is subtracted to calculate a total transmitted amount of infrared from the light source. When multiple wavelengths are used, the light sources are arranged, in the field of view for measurement 713, so as to be at the same location, as another wavelength for comparison, in the machine cross direction (arrow 718), and offset by a certain distance from each other in the machine direction 717. This arrangement is illustrated in FIG. 7B. Unlike the case of a rays, the attenuation curve is drawn with respect to the path length of light. For example, for the absorption wavelength of fibers, the amount of the transmitted light that has been scattered in the paper web due to the fiber weight, vacant spaces, and filler, as illustrated in FIG. 1, is measured. Thus, it is not possible to determine, based on only that signal, which of increase/decrease of the fiber, increase/decrease of the volume (the percentage of the vacant spaces), and increase/decrease of the filler is indicated. Thus, the fiber weight is determined by obtaining the ratio to the signal, referred to as comparative wavelength, that is a similar wavelength and is not absorbed by the fibers. As described above, when β-ray is used, correction for the weight of air is needed, and a correction sensor or correction tool for temperature/gap distance and sensor support frame deformation, etc. that affect the weight of air is required. However, the present device does not require sensors for such correction.

FIG. 9 illustrates a measurement locus of a non-scanning sensor (for example, 700) which characterizes the present invention. The machine direction of the paper web W is indicated by an arrow. The infrared camera captures infrared light that passes through the paper web W that has formation, and, as described above, positional divisions (slices) 902 are formed in the machine cross direction by using software slicing. Reference numeral 901 denotes the length of the measurement area of the paper web at the time of measurement, and the length of the measurement area depends on the shutter time of the camera and the traveling speed of the paper web. In any case, if a sufficient exposure time is ensured for measurement, (for example, 100 milliseconds in a high-speed machine corresponds to a length of 2 m), influence of formation can be sufficiently eliminated. In 100 milliseconds, the scan sensor measures 100 samples, but the movement of the scan sensor in the machine cross direction is only 2 cm. The device according to the present invention performs entire width simultaneous measurement, and for example, if 3 m width is used, the situation is equivalent to providing 300 sensors arranged in the machine cross direction. Reference numeral 903 denotes a measurement locus of the camera at a certain time, and reference numeral 904 denotes a next measurement locus. Although there are some non-measurement areas, such areas can be eliminated when high-speed image processing is performed.

Next, arrangement and configuration of the light source, infrared camera, online sample, etc. used in the present invention will be described. As described above, in the present invention, the basis weight measurement using β-ray which is used in known measurement devices and % moisture measurement using infrared are integrated, and cellulose fibers that are the main component of a paper web and % moisture are measured by using the infrared camera and the infrared light source. In particular, the sensor according to the present invention is optimal for a paper web made of virgin pulp (pure chemical pulp) such as tissue because such a paper web does not contain fillers.

FIGS. 10A to 10C and 10A' to 10C' are schematic diagrams of the infrared LED light source 705 used in the present invention. Two types of light sources are used for different purposes. The light source has a three-tier structure, FIG. 10A is a side view of a light scattering film 1001, FIG. 10B is a side view of a cylindrical lens 1004, and FIG. 10C is a side view of an infrared LED substrate and a heat sink 1006. FIGS. 10A' to 10C' are top views corresponding to FIGS. 10A to 10C, respectively. Infrared LED bulbs 1005 are for different wavelength bands determined depending on the purpose of measurement. The LED substrate 1006 is a module type substrate for allowing easy replacement. The LED bulbs 1005 are arranged at intervals of, for example, 10 mm, but the interval varies depending on the application. The arrangement for the reflection system may be different from the arrangement for the transmission system. The cylindrical lens 1004 produces collimated light as illustrated in the side view. Light is converged in the machine direction and substantially parallel light is produced. When viewed from above, irradiation of light from each LED bulb occurs in a separated manner, as indicated by reference numeral 1003 in FIG. 10B'. By using a film 1001 that diffuses light only in the machine cross direction, as illustrated in the FIG. 10A', the uniform linear light 1002 condensed in the machine direction and shuffled in the machine cross direction can be produced. In this case, divisions in the machine cross direction are formed by slicing the field of view of the camera by using software. Reference numeral 1001 denotes a cross shuffle film, and the linear light 1002 is measured in units of slices separated by software. Such a light source is a standard structure in a defect inspection system using a line CCD camera, and difference is only in the use of an infrared LED bulb instead of a white LED bulb. The light source with a film, for which slicing can be performed freely by using software and uniformity in machine cross direction is achieved, can be handled easier. However, if the film itself is measured, it is required to achieve uniform scattering in the entire surface by using frosted glass or the like instead. This is because in the case of a clear film, there may be no scattering substance that increases path length as compared with transmission absorption.

FIGS. 11A to 11C are schematic diagrams illustrating an arrangement relationship of infrared cameras 1102 to 1106, infrared LED light sources 1112 and 1113, a sample 1107 for online standardization/correction, etc., in measurement by using the transmission type quality parameter measurement device 1100. In a camera beam 1101, for example, five cameras 1102 to 1106 are arranged. Depending on the number of InGaAs elements in the camera, if the measurement width of one pixel is 1 mm, a camera with a field of view of 600 mm or more (for example, 600 pixels×400 pixels) is commercially available. When such a camera is used, in most paper machines, the entire width of the paper web W can be covered by a few to about 20 cameras. Reference numeral 1109 denotes an infrared LED light source frame, reference numeral 1110 denotes an image of an LED bulb, and reference numeral 1107 denotes the sample for online standardization/correction that is placed at the same height as the paper web W and outside the paper web W, which will be described below in detail. Different light sources, such as a multi-wavelength light source 1112 illustrated in FIG. 11B and a single channel light source 1113 illustrated in FIG. 11C, are used depending on the measurement application.

FIGS. 12A and 12B illustrate a configuration of a reflection type quality parameter measurement device 1200 according to another embodiment. In the case of the reflection type, surface coating and % moisture at a surface are measured. Although the total fiber weight and the total water weight cannot be measured by this configuration, the average amount of water existing on the surface portion, the amount of coating, and the like can be accurately measured by using calibration. In addition, accuracy improves compared to measurement by subtracting absolute dry basis weight before application (weight in a dry state without moisture) from absolute dry basis weight after coating, which is a method for measuring an amount of coating originally used for paper machines. After coating, most of water exists at and near the surface and especially in the case of double coating etc., water does not permeates into the inside, and thus the reflection type quality parameter measurement device can measure surface moisture without difference between the front and back surfaces, which is advantage compared to normal transmission type moisture meters. However, the absolute water weight cannot be measured. For example, a combination of a light source 1203 that emits light having an absorption wavelength of water and a light source 1204 that emits light having a comparative wavelength not absorbed by water is used. As in the case of the transmission type, for example, a standard sample 1207 placed at an off-sheet position on the pass line of the paper web can be used as a reference for automatic standardization and correction.

FIGS. 13A to 13C and 14A and 14B illustrate handling of overlap area of cameras for maintaining accuracy and performing online automatic standardization and correction, and online inspection method allowing for check and correction by using, for example, a real web sample and a standard sample at offline positions at both outsides of a paper web, which are essential for the non-scanning type measurement system according to the present invention. In the figure, W denotes a paper web, reference numeral 1301 denotes a field of view of a camera (for example, the camera 1103 in FIG. 11A), and reference numeral 1302 denotes a field of view of an adjacent camera (for example, the camera 1104 in FIG. 11A). Reference numeral 1303 denotes an overlap area, and reference numerals 1321 to 1326 denote arrangement of the LED bulbs or the software slice divisions in the overlap area. Reference numeral 1320 denotes the light source behind the paper web W. FIG. 13A is a diagram of the paper web as viewed from above, FIG. 13C is a graph of light amount pattern upon calibration at the position and a graph of normalized light amount, and FIG. 13B is an example of a graph of light amount upon online measurement. The vertical axis 1304 of the graph indicates the value of the transmitted light amount. The horizontal axis represents slice position in the machine cross direction as in the fields of view 1301 and 1302 of the cameras illustrated in FIG. 13A. In FIG. 13C, reference numeral 1305 denotes a signal graph of the left camera (for example, the camera 1103 in FIG. 11A), and reference numeral 1306 denotes a signal graph of the right camera (for example, the camera 1104 in FIG. 11A). Normally, the scattered transmitted light is emitted in all directions from the surface of the paper web W, and therefore attenuated in inverse proportion to the square of distance from the camera. Thus, a quadratic curve graph attenuated toward the edge of the field of view of the camera is obtained. By normalizing the curves with respect to the center position of the camera (at which the distance becomes shortest and the maximum value is obtained), graphs 1307 and 1308 in FIG. 13C are obtained. The correction is performed pixel by pixel or slice by slice so as to obtain a straight line. Since the calibration was performed using the same sample, the same sample measured value should be obtained for each slice. Thus, in consideration of signal relationship to another camera, offset that gives the same measured value for the same sample for each of the slices of the respective cameras, is recorded. The offset 1310 in FIG. 13B is offset between the measured values in the overlap area, which are obtained online. Checking whether the offset 1310 is the same as the offset 1311 at the time of calibration is performed, and if not, comparison with another adjacent camera to check whether the same offset is obtained is performed, and correction is performed. This determination is made based on the offset of each camera, an estimated value from the measured values for the samples at both sides, a dark count (dark current measurement) by periodically performing online automatic standardization, and the like.

In this standardization and correction method, uniform occurrence in units of cameras, of electrical shifts in each camera, device difference, dirt deposited on the light source during being online, shifts of the field of view of the camera due to thermal distortion, etc., and uniform occurrence of dirt deposition over the entire width on the light source side are premised. However, for partial fluctuation, another diagnosis can be made, because the signal pattern in the camera changes. For example, when dirt is deposited only on a part of the light source, it appears as a sudden change or a peak in a signal in the camera. It is also possible to recognize a case where some of the LED light sources do not emit light due to failure.

FIGS. 14A and 14B illustrate a method for checking measured values using a real web sample 1401 and a standard sample 1402 (corresponding to reference numeral 1107 in FIG. 11A) placed at both outsides of the paper web W, respectively. Each of the samples 1401 and 1402 is placed at the same height as the pass line of the paper web W, and continuously measured online by the cameras at both ends (for example, the cameras 1102 and 1106 in FIG. 11A). The real web sample 1401 is an actual sample sheet of each paper grade. The standard sample 1402 is selected, depending on the application, from samples having a different fiber weight, % moisture, % ash, or the like, and a sample used as a reference for all and made by using synthetic paper or the like that does not exhibit light absorption at any infrared wavelengths, can be used for comparison of difference from initial state in relation to the light source and camera, and does not cause deterioration such as water evaporation. These samples are measured periodically to check whether the sensor (for example, the sensor 700) is in a state in which correct measurement is performed. For example, for measured values for fibers, total average values 1404 and 1406 of the measurement range is measured. Since the calibration is performed using the same sample, it is possible to infer from a change of this value that there is fluctuation on the camera side or light source side, or there is dust such as dirt or paper dust between the camera and the light source. Therefore, for example, if there is a difference of 1 g, an offset of 1 g is given to a measured value 1405 of each camera as an online dynamic correction value. As long as the cameras at both ends checked by using the actual sample (for example, the cameras 1102 and 1106 in FIG. 11A) are in good condition, by checking for the overlap areas with cameras adjacent in the direction of the center of the web (for example, the cameras 1103 and 1105 in FIG. 11A), it can be considered that all the rest of cameras (for example, the cameras 1103 to 1105 in FIG. 11A) have been checked indirectly. As a result, it is possible to perform online automatic standardization and correction to establish accuracy, which is not addressed by conventional methods. It is possible to present a new method for non-scanning camera system in which automatic standardization cannot be performed offline due to the fixed sensor and thus the condition of the sensor can be checked only upon the off-sheet state due to machine shutdown or sheet break. As described above, one of reasons why the prior art came to a standstill is that infrared cameras were expensive and short-lived halogen lamps were used because the infrared LED had not yet been available as general-purpose products, and thus frequent sensor standardization is required. Thus, a similar method to the present method can be used even when a line sensor is used, the present method can be applied to the conventional method, and the present method can be applied to a case where halogen must be used.

FIG. 15 is a schematic diagram illustrating a quality parameter measurement device 1500 according to another embodiment. FIG. 15 illustrates a case of a completely overlapped configuration in which an overlap area 1501 of the fields of view of cameras, which is required to maintain accuracy in the non-scanning measurement according to the present invention, is extended to the center of the field of view of adjacent camera so that each of the fields of view for the entire paper web W can be measured by two adjacent cameras. However, both ends do not need to be overlapped.

FIGS. 16A and 16B are schematic diagrams of a quality parameter measurement device 1600 according to another embodiment. In the quality parameter measurement device 1600, a reflection infrared light source 1601 is provided in a partial area in a transmission type measurement device (for example, the measurement device 1100 in FIG. 11A), the same area camera 1603 measures reflected infrared light from the light source 1601 as the reflection wavelength, simultaneously with transmitted infrared light from a three-wavelength light source 1602, and by performing comparison for transmission signal ratio, the total light amount of each wavelength, and the total light amount of the reflection light source, difference in % ash is measured. Of course, the ratio between transmission and reflection at the time of calibration is used as the reference. The light source 1602 is an infrared LED light source that emits light having the absorption wavelength of fibers, the absorption wavelength of water, and a comparative wavelength, and the infrared LED light source 1601 emits light having a comparative wavelength that is not absorbed by the materials constituting the paper web. The camera 1603 for the measurement is arranged so that three light sources for transmitted light and one light source for reflected light can be observed within the same field of view, and measured values are sent to a system computer (not illustrated). Conversely, without using a reflection infrared light source, one additional camera may be provided on the same side as the transmission infrared light source with respect to the paper web W and continuous measurement for the reflection surface may be performed. A method to be used may be determined based on available space at manufacturing site.

FIGS. 17A and 17B illustrate the concept of measuring % ash. For paper webs W manufactured as the same paper grade, if waste paper generated due to failure in mixing ratio or another reason is added to the raw material and thus mixing ratio of pulp containing ash changes, then as a result, % ash changes and thus the ratio between the transmitted light and the reflected light changes. In known measurement devices, % ash is measured and controlled by using X-rays and a sensor using the same principle as that of the basis weight sensor. X-rays have the property of being sensitive to ash, which is an inorganic substance, and less sensitive to fibers, which are organic substances. The original purpose of the ash is to prevent an optical weakness called strike-through which means that characters printed on the back side of the paper is visible through the paper as seen from the front side. The ash is added as an additive, and by increasing scattering of light, it blocks light from the front side to prevent strike-through and prevents light from the back side from being transmitted to the front side. Thus, ash is essentially a substance for changing an optical property. However, the weight ratio of ash has been measured using X-rays, because there is no good sensor other than this indirect method. In the measurement method of the present invention, in order to measure the essential optical property, as an application of the fiber and moisture measurement device using infrared, % ash is measured by performing comparison for the transmitted component, the reflected component, and the absorption component by fibers. Measurement is performed by calibration with samples collected in different states in advance. A paper web 1706 of FIG. 17A has low ash content. Emitted infrared 1701 having a comparative wavelength is repeatedly scattered and reflected inside the paper web 1706. Transmitted light 1703 that has not been absorbed by the fibers is measured by a camera 1704, and reflected light 1702 that has been emitted by a light source 1705 and then reflected is also measured by the camera 1704. A paper web 1716 of FIG. 17B has high ash content. The same emitted infrared 1701 having the comparative wavelength is more repeatedly scattered and reflected inside the paper web 1716. Both transmitted light 1713 and reflected light 1712 that has been emitted by the light source 1705 and then reflected are measured by the camera 1704. As indicated by the thickness of the arrows, when % ash is high, the transmitted light decreases and the reflected light increases (1702÷1703<1712÷1713). The value obtained by dividing each of the measured values by the measured value of the standard sample represents the degree of influence of % ash on the amount of transmitted and reflected light due to the difference in the mixing ratio. If calibration is performed in advance using these measured values for standard samples having different % ash, it is possible to perform an optimal light strike-through degree measurement without measuring the ash weight. Taking into consideration the current status of usage of ash sensors, it is more economical to measure optical characteristics with this sensor, roughly control the ash input amount so as to make the input amount as small as possible, and increase the fiber weight instead.

Figure 8A:
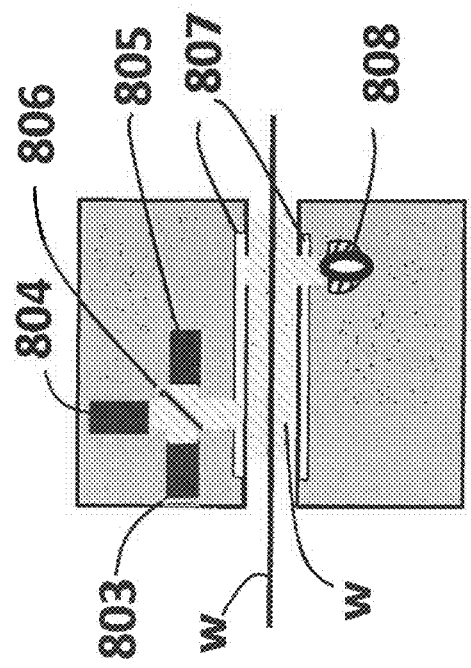
FIG. 8A is a photograph of formation of a paper web W.
Figure 8B:
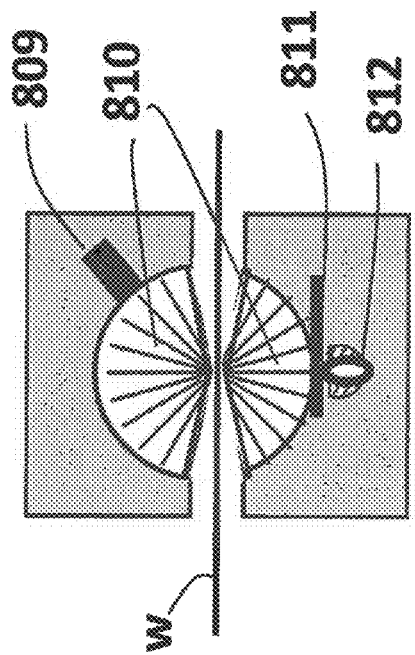
FIG. 8B is a structural diagram of a moisture meter using an infinite random scattering method.
Figure 8C:
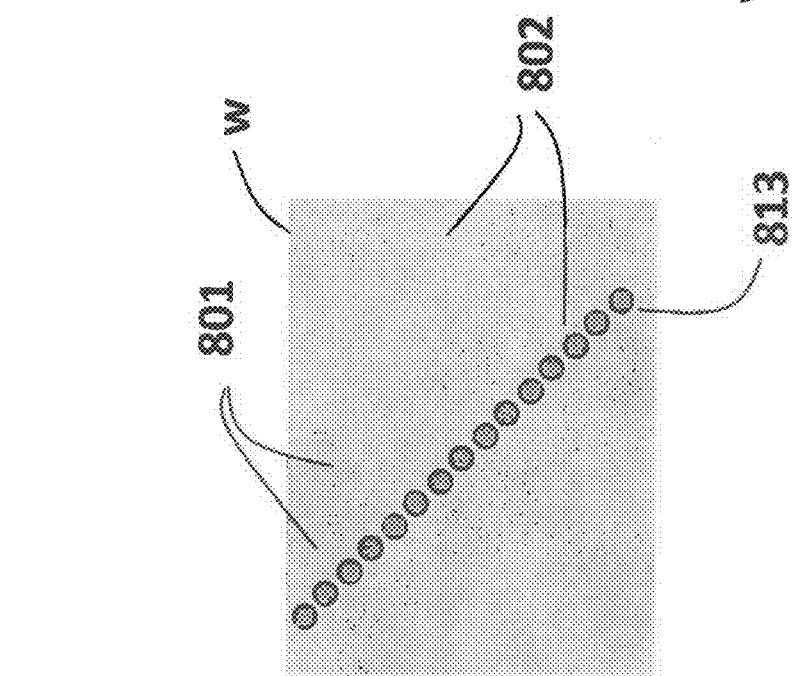
FIG. 8C is a structural diagram of an integrating hemisphere type moisture meter.

Recent paper machines are mostly dedicated for some paper grade that always produce the same paper grade or paper grades having slightly different basis weights, such as tissue, newsprint, copy paper, printing paper, liner board, and corrugating medium. This is a trend mainly in, for example, strategy of machine intensiveness for improving production efficiency in major companies, but conversely, small and medium-sized companies tend to use specialized paper machines for making special paper. The ability to produce any kind of paper leads to increase in complexity of machines, inefficiency relating to pulp blending, addition of chemicals, etc., and, in addition leads to complicated operating conditions and increase in human error. Therefore, in the latest machines that manage paper grade by using DCS, pulp blending and percentages of the mixed chemicals and fillers are also measured and controlled so as to be kept within a certain fluctuation range. By performing calibration using paper obtained under such paper grade management, on the premise that change in light path length due to the mixing ratio is minimal (which may cause a change in a measured value), the fiber measurement and % moisture measurement described above can be performed. Conventionally, since the mixing ratio is unknown and there is sufficient fluctuation, for example, methods to make optical path length infinite, such as an infinite random scattering method and an integrating hemisphere type method (see FIGS. 8B and 8C), are used for the mixing ratio fluctuation. A correction method based on the amount of transmitted light and the like was patented 50 years ago as a correction sensor for such a direct reading type infrared sensor, as a prior art. In the present invention, a method of performing a periodic correction using the total light amount of each of the transmitted and reflected light, each ratio, comparison with a standard sample, and the like, as described above is also used, but paper made by using virgin pulp, such as tissue do not include additives at all and thus there is no need for these corrections. However, it is a necessary technique for improving the absolute value accuracy for a paper made by using ash or recycled pulp, as a single sensor.

On the other hand, at manufacturing site where QCS has already been introduced, it is thought that the present invention can be used easier by arranging the sensor as upstream as possible and upstream of the surface coating (position of base sheet including only internal additives after mixing of additives), suppressing fluctuations mainly by using the high-speed measurement control in the machine direction and the machine cross direction, and checking the final quality with the existing QCS. In this case, it is desirable to allow the accuracy of the final measured value to rely on the existing basis weight sensor and moisture sensor, and perform cascade control (upstream control) for long-term fluctuations. A method in which measurement with a fixed sensor without scanning is performed, positional correspondence with respect to the present measurement device is determined, and such measurement is performed over the full width also can contribute to cost cutting. Thus, in the future, design in consideration of such integration with existing technologies will be needed.

Figure 18:
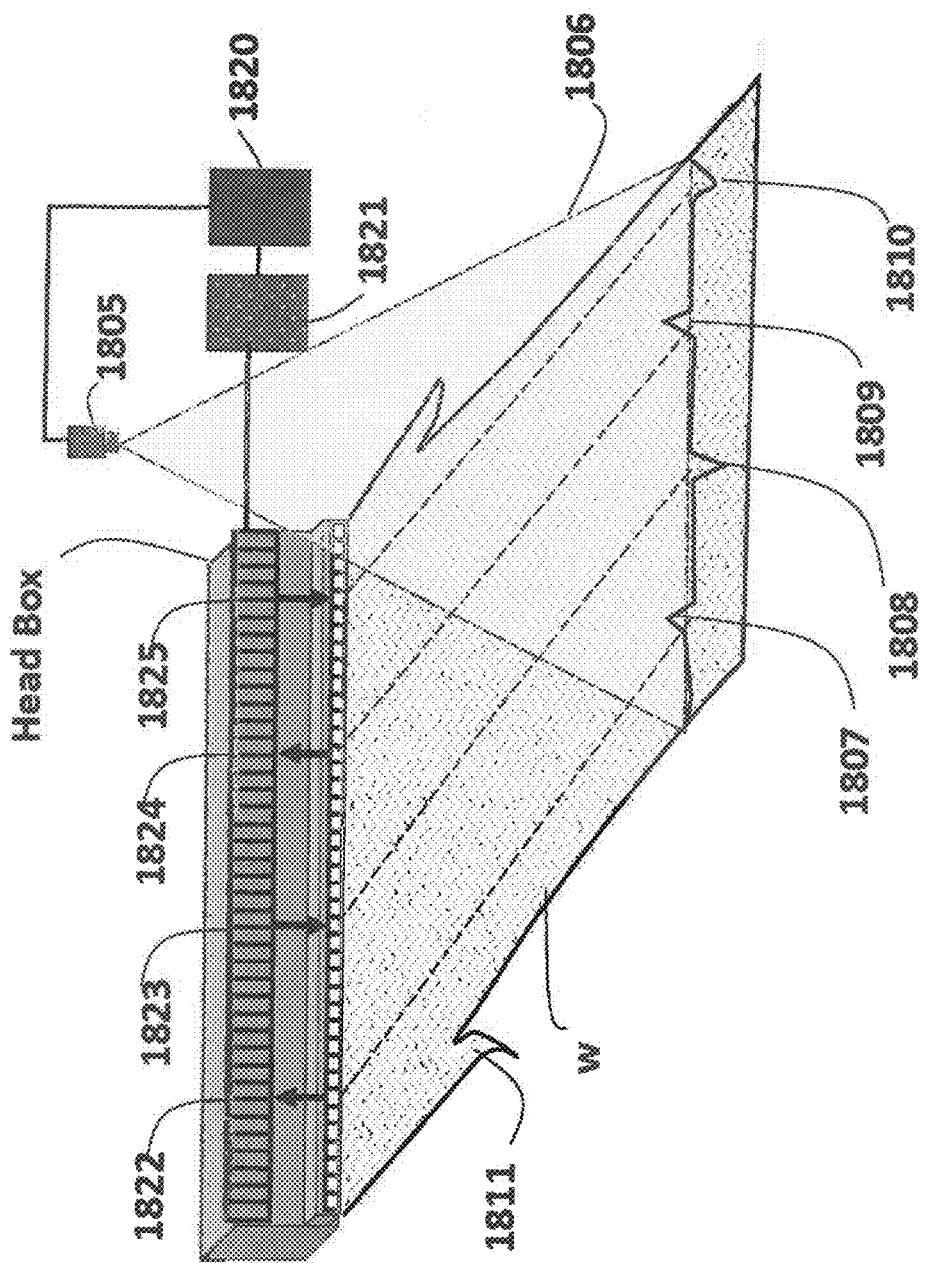
FIG. 18 is a schematic diagram of a method of testing for shrinkage and wander in the paper web W.

FIG. 18 illustrates a method for determining correspondence between each of the slice positions of a head box as a control point and slice positions in a camera 1805 as a measurement point, when the above-described non-scanning type measurement device (for example, the measurement device 1100 in FIG. 11A) is used in a paper machine (see FIG. 2). After the paper web W is formed with a wire, an edge portion 1811 is cut off by a water shower (not illustrated). Since the edge portion 1811 is not uniform, such a process is necessary. Therefore, the width of the slurry supplied from the head box is reduced at both edges thereof by several centimeters to a dozen of centimeters, after the forming, and then the paper web W is subjected to the press and drying process. Since the paper shrinks in the drying step, the widths of the paper, from the upstream side, at the head box, after trimming of paper edges, and after the drying step prior to the winding are different from each other. In addition, the pattern of shrinkage is not uniform in the machine cross direction but usually a bowl shape. If wander occurs additionally, it becomes impossible to accurately determine the number of the actuator of the head box corresponding to a measurement point upstream of winding, and as a result, a new error is generated by feedback control. The well-known sawtooth profile is thus created.

An infrared camera 1805 measures the fiber weight of the paper web W in a field of view 1806. Assuming that reel change is about to begin at the winder, a part of the paper web W having a length of several tens of meters before the reel change is wound as top layers of the wound roll, a few to a dozen of which are peeled off for visual inspection. In addition, it cannot be offered for sale since it is wrinkled because of being wound as lowermost layers at the next process, and thus treated as a waste paper for these two reasons. Accordingly, for the part, there is no problem in performing a bump test (output response test) in which output of the actuator in the machine cross direction of the paper is changed to cause a change in the weight of the paper. In the existing measurement control system, this method can be performed only upon paper grade change, which takes several tens of minutes and during which all the paper becomes waste paper. This is not appropriate in terms of the original purpose, because paper shrinkage and wander change during the paper grade change. However, there was no other way because it takes a dozen of minutes or more to acquire feedback of the sensor from a step response, due to use of scanning. In the method of the present invention, measurement for the step response includes only a machine delay, and thus, a result can be obtained in about 10 seconds. This is achieved by the high speed measurement, which is the greatest advantage of the non-scanning system. The measured value of the camera 1805 is recorded before the reel change, and a measurement control system 1820 connected to the camera 1805 transmits, to an actuator controller 1821, an increase or decrease signal for a plurality of actuators such as slices 1822, 1823, 1824, and 1825, as illustrated in the figure. After time corresponding to the machine delay, the camera measures and records fluctuations 1807, 1808, 1809, and 1810 corresponding to the increase or decrease signal. This is called a bump test. The peak values before and after the output change are measured, and the position of the actuator, a pattern due to shrinkage in the drying step, and an offset due to wander are measured.

As a result, it is possible to completely prevent control failure and error diffusion in the machine cross direction due to incorrect correspondence between the measurement points and the control points, and thus to manufacture a more uniform paper web. Slow response in measurement and error diffusion due to position offsets caused by irregular actuator pitch, which are the biggest weaknesses of known systems, are the limits of current papermaking technology, and thus by overcoming them, it is possible to contribute improvement of quality and productivity in all aspects.

In the present invention, filtering, which is a fatal drawback of the scanning sensor, is not required, an operator action can be visually recognized in several tens of seconds, and a slight % moisture fluctuation caused by a malfunction of a high-speed rotating machine equipment can be observed. To check them, it is not necessary to perform conversion to an engineering unit, that is, g/ms as a basis weight or % moisture, and it is sufficient to show a change of basic light amount distribution. Therefore, by performing measurement at high speed without a sufficient exposure time (803 in FIG. 8B) in the measurement mode and mapping seamless light amounts, a % moisture unevenness map can be formed. By synchronizing the map with the rotational speed of each equipment, the equipment causing the problem can be identified. In addition, by providing a high-speed measurement dedicated camera that monitors only a specific area, providing a high-speed fluctuation monitoring mode, logging only raw signals for a few minutes, and performing a fast Fourier transform (FFT), it is possible to obtain a power spectrum of high-speed fluctuation in the machine direction and perform process analysis.

As described above, currently, performance of machine equipment, such as a wire (several meters to tens of meters), a press roll (perimeter 2 to 3 meters), felt (several meters to tens of meters), and canvas (several meters to tens of meters), cannot be observed with the scanning sensor. However, change in such performance can be detected by using the high-speed measurement method according to the present invention, and thus a quick response is possible. Thus, it can be expected to achieve various economic effects such as reduction of unnecessary energy and prevention of sheet break, reduction of chemicals, improvement of productivity, improvement of maintainability, and extension of equipment change cycle.

REFERENCE SIGNS LIST

W: Paper web (long sheet material)
700: Non-scanning sensor
702: Infrared camera
705: Infrared light source
1100: Quality measurement device
1107: Real web sample
1108: Standard sample

The invention claimed is:

1. A quality parameter measurement device for a long sheet material that measures, by using an infrared light source and an infrared camera configured to receive infrared, a quality parameter of the long sheet material moving toward a winder, wherein
   a plurality of the infrared light sources and a plurality of the infrared cameras are arranged in the machine cross direction so as to cover the entire width of the long sheet material, and fields of view of adjacent infrared cameras overlap each other,
   the infrared camera is an infrared area camera,
   a plurality of the infrared light sources, each configured to emit infrared having a different wavelength, are arranged in the machine direction, and
   the plurality of infrared light sources are arranged so that infrared emitted from each of the plurality of infrared light sources and traveling via the long sheet material is measured simultaneously at the same infrared area camera, and so that irradiation areas of the plurality of infrared light sources do not overlap each other.

2. The quality parameter measurement device for a long sheet material according to claim 1, further comprising a reference sample, including a real web sample and a standard sample, wherein
   the reference sample is placed in an extension plane of the long sheet material in the machine cross direction so that the reference sample and the long sheet material are irradiated with infrared from the same infrared light source and so that infrared traveling via the reference sample and infrared traveling via the long sheet material are measured simultaneously at the same infrared camera.

3. A quality parameter measurement method for a long sheet material, comprising:
   measuring a quality parameter of the long sheet material by using the quality measurement device for a long sheet material according to claim 1.

4. A quality parameter measurement method for a long sheet material, comprising:
   by using the quality measurement device for a long sheet material according to claim 1, receiving, by the infrared camera, transmitted infrared and reflected infrared emitted from the infrared light source and traveling via the long sheet material; and measuring a light scattering ratio of the long sheet material, based on transmittance calculated based on the received transmitted infrared intensity and the received reflected infrared intensity.

5. A quality control method for a long sheet material, comprising:

determining, based on the light scattering ratio acquired by using the measurement method according to claim 4, whether attenuation in the transmitted infrared intensity is caused by fibers or ash, to perform determination for correction of either or both of fiber weight and water weight as quality parameters, relating to light path length or determination for process condition change.

6. A quality control method for a long sheet material, comprising:

by using the quality measurement device for a long sheet material according to claim 1, synchronously with a reel change for a wound roll in the winder, while changing either or both of fiber weight and water weight as quality parameters at a predetermined cross direction control point and by a predetermined amount;

performing simultaneous measurement, for the entire width of the long sheet material, of a quality parameter of the long sheet material moving toward a winder, by using the infrared light source configured to irradiate the long sheet material and the infrared camera configured to receive infrared traveling via the long sheet material; and based on a measured value acquired, checking positional relationship between a measurement point and the cross direction control point for either or both of basis weight control or water weight control, which has changed due to at least one of shrinkage and wander in the machine cross direction of the long sheet material being wound.

* * * * *